(12) United States Patent
Lab et al.

(10) Patent No.: US 8,388,659 B1
(45) Date of Patent: Mar. 5, 2013

(54) SPONDYLOLISTHESIS SCREW AND INSTRUMENT FOR IMPLANTATION

(75) Inventors: Eric A. Lab, Wadsworth, OH (US); Mukund Gundanna, College Station, TX (US)

(73) Assignee: Theken Spine, LLC, Akron, OH (US)

( * ) Notice: Subject to any disclaimer, the term of this patent is extended or adjusted under 35 U.S.C. 154(b) by 544 days.

(21) Appl. No.: 12/589,160

(22) Filed: Oct. 19, 2009

Related U.S. Application Data

(60) Provisional application No. 61/106,387, filed on Oct. 17, 2008, provisional application No. 61/147,687, filed on Jan. 27, 2009, provisional application No. 61/147,695, filed on Jan. 27, 2009.

(51) Int. Cl.
*A61B 17/70* (2006.01)
(52) U.S. Cl. ........ 606/265; 606/266; 606/267; 606/305; 606/306; 606/307
(58) Field of Classification Search .......... 606/266–270, 606/305–308, 92–94
See application file for complete search history.

(56) References Cited

U.S. PATENT DOCUMENTS

| | | |
|---|---|---|
| 4,611,581 A | 9/1986 | Steffee |
| 5,281,223 A | 1/1994 | Ray |
| 5,352,231 A | 10/1994 | Brumfield et al. |
| 5,385,565 A | 1/1995 | Ray |
| 5,534,001 A | 7/1996 | Schlapfer et al. |
| 5,591,165 A | 1/1997 | Jackson |
| 5,603,714 A | 2/1997 | Kaneda et al. |
| 5,649,931 A | 7/1997 | Bryant et al. |
| 5,697,929 A | 12/1997 | Mellinger |
| 5,720,751 A | 2/1998 | Jackson |
| 5,860,983 A | 1/1999 | Wenstrom, Jr. |
| 5,879,350 A | 3/1999 | Sherman et al. |
| 5,885,286 A | 3/1999 | Sherman et al. |
| 5,910,141 A | 6/1999 | Morrison et al. |
| 5,941,885 A | 8/1999 | Jackson |
| 5,980,523 A | 11/1999 | Jackson |
| 6,004,349 A | 12/1999 | Jackson |
| 6,053,917 A | 4/2000 | Sherman et al. |
| 6,056,753 A | 5/2000 | Jackson |
| 6,059,786 A | 5/2000 | Jackson |
| 6,077,262 A | 6/2000 | Schlapfer et al. |
| 6,086,589 A | 7/2000 | Kuslich et al. |
| 6,102,913 A | 8/2000 | Jackson |
| 6,102,914 A | 8/2000 | Bulstra et al. |
| 6,139,549 A | 10/2000 | Keller |
| 6,179,841 B1 | 1/2001 | Jackson |
| 6,183,472 B1 | 2/2001 | Lutz |
| 6,189,422 B1 | 2/2001 | Stihl |
| 6,224,596 B1 | 5/2001 | Jackson |
| 6,236,875 B1 | 5/2001 | Bucholz et al. |
| 6,248,105 B1 | 6/2001 | Schlapfer et al. |
| 6,248,107 B1 | 6/2001 | Foley et al. |
| 6,251,111 B1 | 6/2001 | Barker et al. |
| 6,287,313 B1 | 9/2001 | Sasso |
| 6,379,356 B1 | 4/2002 | Jackson |

(Continued)

FOREIGN PATENT DOCUMENTS

WO 2008039247 A2 4/2008

*Primary Examiner* — Andrew Yang
(74) *Attorney, Agent, or Firm* — Middleton Reutlinger; Robert H. Eichenberger; Chad D. Bruggeman

(57) ABSTRACT

A screw for use in spinal surgery provided with a screw shaft and a screw head and at least one extension tab extending proximally from the screw head, the extension tab being defined relative to the screw head by a stress concentration feature. At a proximal end of the extension tab, the extension tab may be narrower in a circumferential direction than the extension tab at a distal portion thereof. A particular shape of stress concentration may be provided.

18 Claims, 27 Drawing Sheets

Radially inner    Radially outer

U.S. PATENT DOCUMENTS

| | | |
|---|---|---|
| 6,415,693 B1 | 7/2002 | Simon et al. |
| 6,440,132 B1 | 8/2002 | Jackson |
| 6,440,133 B1 | 8/2002 | Beale et al. |
| 6,454,768 B1 | 9/2002 | Jackson |
| 6,475,218 B2 | 11/2002 | Gournay et al. |
| 6,530,929 B1 | 3/2003 | Justis et al. |
| 6,562,046 B2 | 5/2003 | Sasso |
| 6,616,663 B2 | 9/2003 | Glenn, III et al. |
| 6,648,888 B1 | 11/2003 | Shluzas |
| 6,660,006 B2 | 12/2003 | Markworth et al. |
| 6,709,434 B1 | 3/2004 | Gournay et al. |
| 6,716,214 B1 | 4/2004 | Jackson |
| 6,726,687 B2 | 4/2004 | Jackson |
| 6,726,689 B2 | 4/2004 | Jackson |
| 6,726,692 B2 | 4/2004 | Bette |
| 6,730,089 B2 | 5/2004 | Jackson |
| 6,740,086 B2 | 5/2004 | Richelsoph |
| 6,740,089 B2 | 5/2004 | Haider |
| 6,743,231 B1 | 6/2004 | Gray et al. |
| 6,746,449 B2 | 6/2004 | Jones et al. |
| 6,783,527 B2 | 8/2004 | Drewry et al. |
| 6,790,209 B2 | 9/2004 | Beale et al. |
| 6,858,031 B2 | 2/2005 | Morrison et al. |
| 6,860,889 B2 | 3/2005 | Bonati et al. |
| 6,884,244 B1 | 4/2005 | Jackson |
| 6,911,030 B1 | 6/2005 | Vanacker et al. |
| 6,997,927 B2 | 2/2006 | Jackson |
| 7,004,947 B2 | 2/2006 | Shluzas et al. |
| 7,008,422 B2 | 3/2006 | Foley et al. |
| 7,011,660 B2 | 3/2006 | Sherman et al. |
| 7,073,415 B2 | 7/2006 | Casutt et al. |
| 7,090,679 B2 | 8/2006 | Saint-Martin et al. |
| 7,139,601 B2 | 11/2006 | Bucholz et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,186,255 B2 * | 3/2007 | Baynham et al. ............. 606/266 |
| 7,188,554 B2 | 3/2007 | Baynham |
| 7,188,626 B2 | 3/2007 | Foley et al. |
| 7,204,838 B2 | 4/2007 | Jackson |
| 7,226,453 B2 | 6/2007 | Chao et al. |
| 7,250,052 B2 | 7/2007 | Landry et al. |
| 7,261,714 B2 | 8/2007 | Richelsoph |
| 7,278,995 B2 | 10/2007 | Nichols et al. |
| 7,306,603 B2 | 12/2007 | Boehm, Jr. et al. |
| 7,322,980 B2 | 1/2008 | Roussouly et al. |
| 7,341,594 B2 | 3/2008 | Shluzas et al. |
| 7,371,239 B2 | 5/2008 | Dec et al. |
| 7,434,325 B2 | 10/2008 | Foley et al. |
| 7,470,279 B2 | 12/2008 | Jackson |
| 7,476,239 B2 | 1/2009 | Jackson |
| 7,513,905 B2 | 4/2009 | Jackson |
| 7,563,264 B2 | 7/2009 | Landry et al. |
| 7,611,526 B2 | 11/2009 | Carl et al. |
| 7,618,440 B2 | 11/2009 | Gray et al. |
| 7,621,918 B2 | 11/2009 | Jackson |
| 7,625,396 B2 | 12/2009 | Jackson |
| 7,648,521 B2 | 1/2010 | Hestad |
| 7,651,502 B2 | 1/2010 | Jackson |
| 7,662,175 B2 | 2/2010 | Jackson |
| 7,678,139 B2 | 3/2010 | Garamszegi et al. |
| 7,699,852 B2 * | 4/2010 | Frankel et al. ................. 606/92 |
| 7,717,944 B2 | 5/2010 | Foley et al. |
| 7,758,617 B2 | 7/2010 | Iott et al. |
| 7,763,055 B2 | 7/2010 | Foley |
| 7,776,067 B2 | 8/2010 | Jackson |
| 7,789,896 B2 | 9/2010 | Jackson |
| 7,794,477 B2 | 9/2010 | Melkent et al. |
| 7,824,413 B2 | 11/2010 | Varieur et al. |
| 7,833,250 B2 | 11/2010 | Jackson |
| 7,842,073 B2 | 11/2010 | Richelsoph et al. |
| 7,846,187 B2 | 12/2010 | Jackson |
| 7,854,751 B2 | 12/2010 | Sicvol et al. |
| 7,862,595 B2 | 1/2011 | Foley |
| 7,867,259 B2 | 1/2011 | Foley et al. |
| 7,875,031 B2 | 1/2011 | Chin et al. |
| 7,887,539 B2 | 2/2011 | Dunbar, Jr. et al. |
| 7,887,548 B2 | 2/2011 | Usher, Jr. et al. |
| 7,967,821 B2 | 6/2011 | Sicvol et al. |
| 8,052,720 B2 | 11/2011 | Kuester et al. |
| 2002/0058942 A1 | 5/2002 | Biedermann et al. |
| 2002/0133159 A1 | 9/2002 | Jackson |
| 2003/0040746 A1 | 2/2003 | Mitchell et al. |
| 2005/0049589 A1 | 3/2005 | Jackson |
| 2005/0182410 A1 | 8/2005 | Jackson |
| 2005/0187549 A1 | 8/2005 | Jackson |
| 2005/0228379 A1 | 10/2005 | Jackson |
| 2005/0267477 A1 | 12/2005 | Jackson |
| 2005/0277934 A1 | 12/2005 | Vardiman |
| 2006/0009773 A1 | 1/2006 | Jackson |
| 2006/0025771 A1 | 2/2006 | Jackson |
| 2006/0036259 A1 | 2/2006 | Carl et al. |
| 2006/0058794 A1 | 3/2006 | Jackson |
| 2006/0069391 A1 | 3/2006 | Jackson |
| 2006/0184178 A1 | 8/2006 | Jackson |
| 2006/0200135 A1 | 9/2006 | Sherman et al. |
| 2006/0200136 A1 | 9/2006 | Jackson |
| 2006/0217735 A1 | 9/2006 | MacDonald et al. |
| 2006/0229614 A1 | 10/2006 | Foley et al. |
| 2006/0241602 A1 | 10/2006 | Jackson |
| 2006/0241603 A1 | 10/2006 | Jackson |
| 2006/0264934 A1 | 11/2006 | Fallin |
| 2006/0293664 A1 | 12/2006 | Schumacher |
| 2006/0293680 A1 | 12/2006 | Jackson |
| 2007/0123989 A1 | 5/2007 | Gfeller et al. |
| 2007/0129731 A1 | 6/2007 | Sicvol et al. |
| 2007/0179502 A1 | 8/2007 | Raynor et al. |
| 2007/0191840 A1 | 8/2007 | Pond, Jr. et al. |
| 2007/0233079 A1 | 10/2007 | Fallin et al. |
| 2007/0270806 A1 | 11/2007 | Foley et al. |
| 2007/0270816 A1 | 11/2007 | Rezach |
| 2007/0288003 A1 | 12/2007 | Dewey et al. |
| 2007/0288026 A1 | 12/2007 | Shluzas |
| 2007/0299444 A1 | 12/2007 | DiPoto et al. |
| 2008/0009864 A1 | 1/2008 | Forton et al. |
| 2008/0015584 A1 | 1/2008 | Richelsoph |
| 2008/0039844 A1 | 2/2008 | Jackson |
| 2008/0077139 A1 | 3/2008 | Landry et al. |
| 2008/0082103 A1 | 4/2008 | Hutton et al. |
| 2008/0114403 A1 | 5/2008 | Kuester et al. |
| 2008/0119849 A1 | 5/2008 | Beardsley et al. |
| 2008/0119850 A1 | 5/2008 | Sicvol et al. |
| 2008/0119852 A1 | 5/2008 | Dalton et al. |
| 2008/0125788 A1 | 5/2008 | Cohen et al. |
| 2008/0221583 A1 | 9/2008 | Sharifi-Mehr et al. |
| 2008/0221626 A1 | 9/2008 | Butters et al. |
| 2008/0234678 A1 | 9/2008 | Gutierrez et al. |
| 2008/0275456 A1 | 11/2008 | Vonwiller et al. |
| 2008/0300638 A1 | 12/2008 | Beardsley et al. |
| 2009/0198273 A1 | 8/2009 | Zhang et al. |
| 2009/0228052 A1 | 9/2009 | Beardsley et al. |
| 2009/0234392 A1 | 9/2009 | Dziedzic et al. |
| 2010/0174325 A1 | 7/2010 | Won et al. |
| 2011/0040335 A1 | 2/2011 | Stihl et al. |
| 2011/0178560 A1 | 7/2011 | Butler et al. |
| 2011/0196429 A1 | 8/2011 | Hua |
| 2011/0202095 A1 | 8/2011 | Semler et al. |
| 2011/0213419 A1 | 9/2011 | Richelsoph |
| 2011/0301647 A1 | 12/2011 | Hua |

\* cited by examiner

REGION OF
INTERFERENCE
(BEFORE REDUCTION)

REGION OF
INTERFERENCE
(AFTER REDUCTION)

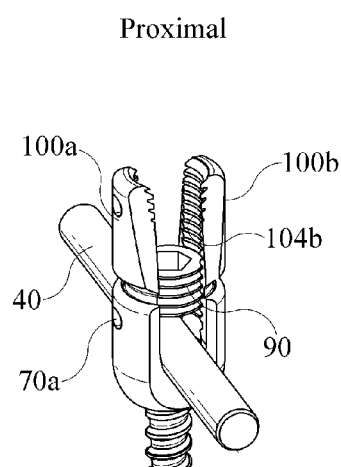
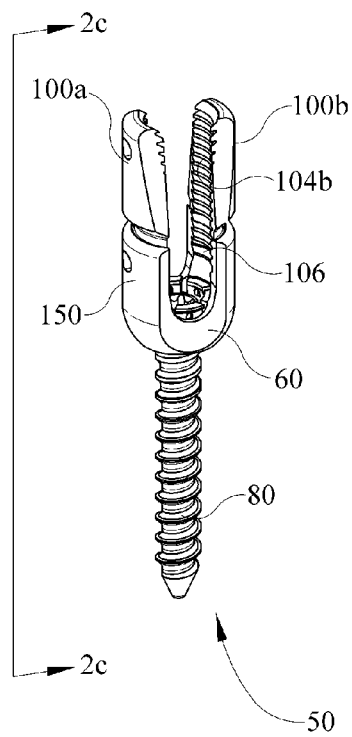
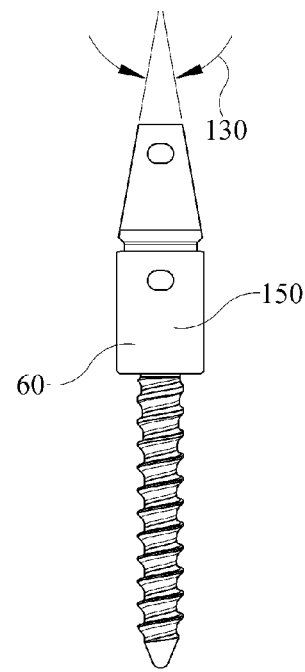
FIG. 2A
FIG. 2B
FIG. 2C

Radially inner    Radially outer

PROXIMAL

DISTAL   Figure 3B    Figure 3C

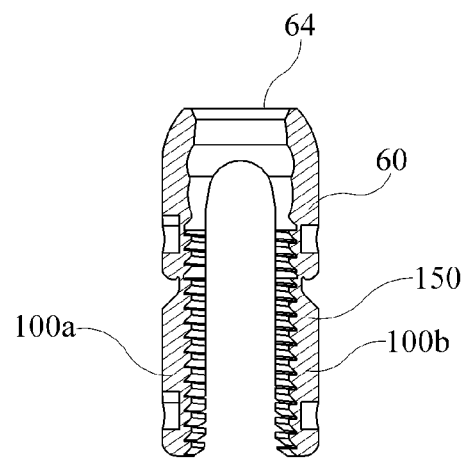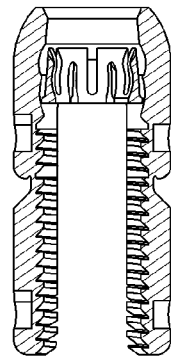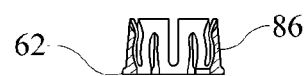
Figure 9A
Figure 9B
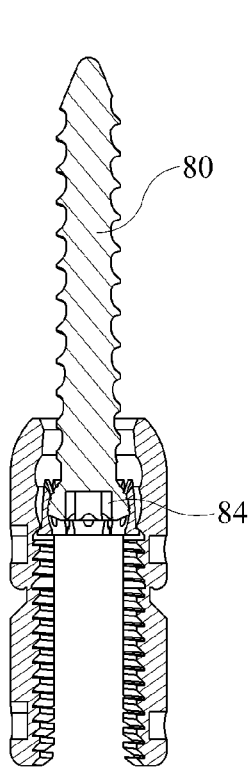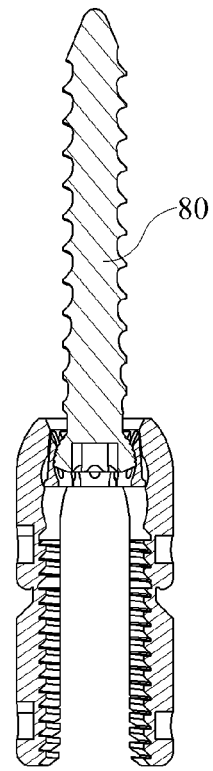
Figure 9C
Figure 9D

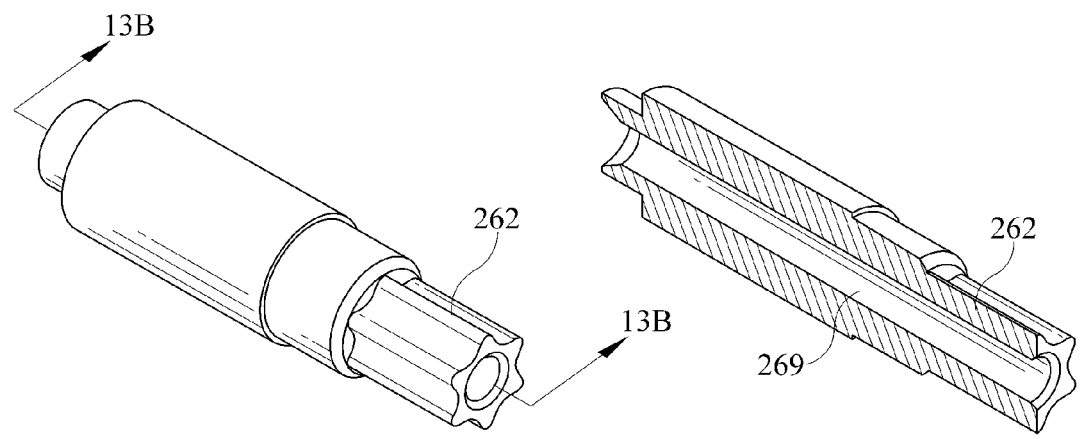
Figure 13A
Figure 13B
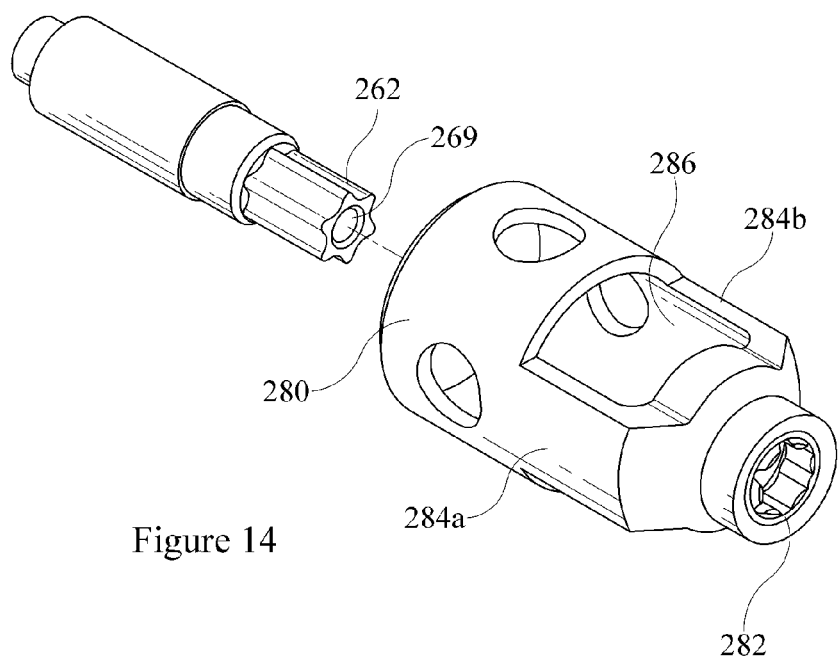
Figure 14

See Figure 18a

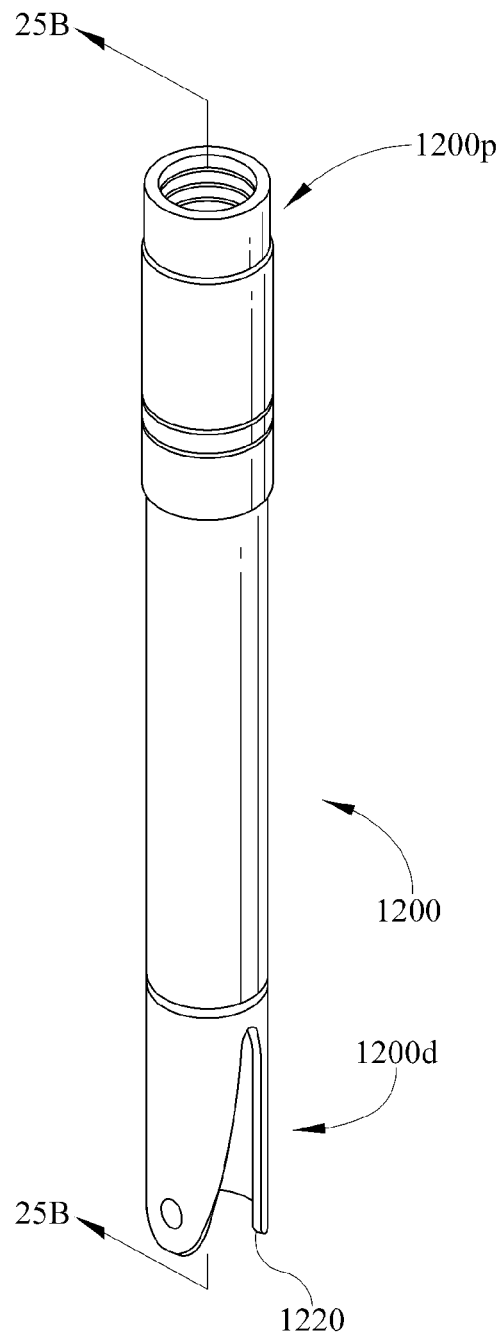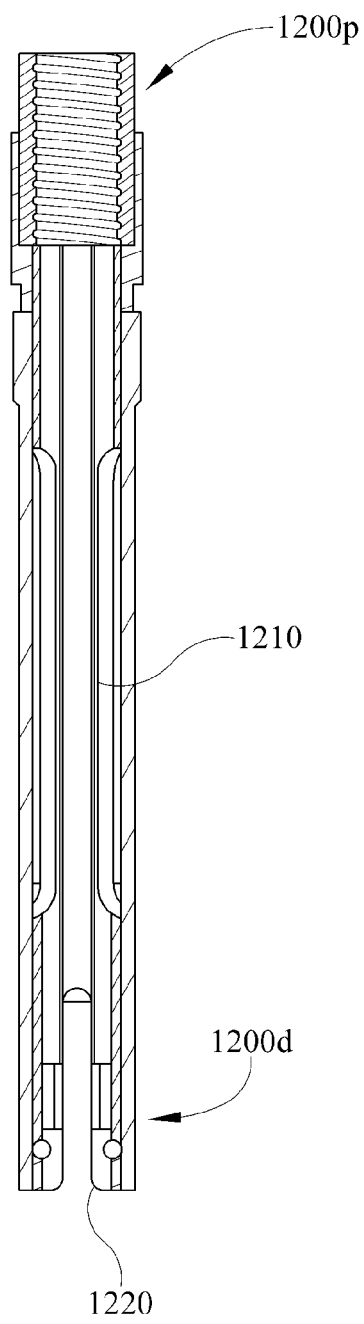
Figure 25A
Figure 25B

SPONDYLOLISTHESIS SCREW AND INSTRUMENT FOR IMPLANTATION

CROSS-REFERENCE TO RELATED APPLICATIONS

This application claims priority to and benefit under 35 U.S.C. §119(e) to U.S. Provisional App. No. 61/106,387, filed on Oct. 17, 2008; U.S. Provisional App. No. 61/147,687, filed on Jan. 27, 2009; and U.S. Provisional App. No. 61/147,695, filed on Jan. 27, 2009. The entire contents of the aforementioned applications are hereby incorporated by reference.

TECHNICAL FIELD

The invention pertains to spinal surgery.

BACKGROUND

Pedicle screws and spinal rods are frequently used to stabilize or re-shape a spine. For the treatment of spondylolisthesis and similar conditions requiring reducing bony structures that are out of position, sometimes pedicle screws are made that have heads that contain internally threaded extension tabs that are longer than the ultimately desired dimensions of the screw head. A setscrew can be engaged with the extension tabs and can be used to urge a spinal rod and a pedicle screw toward each other.

SUMMARY

In embodiments of the invention, there are provided pedicle screws that have extension tabs that can be broken off from the main body of the pedicle screw, in which the tabs have a taper. Embodiments of the invention can include a stress concentration feature having an undercut configuration, so as to promote creation of a fracture surface that is at least somewhat recessed in relation to nearby smooth surfaces. Embodiments of the invention may include an axisymmetric groove on the threaded interior as a stress concentration feature. Embodiments of the invention can also include a frictional collet, a central hole, or fenestration holes. These various features may be combined in any combination.

Embodiments of the invention may include an instrument for grasping or installation of pedicle screws. The instrument may be capable of engaging a pedicle screw directly from a tray, with only a gross alignment with the overall slot in the pedicle screw. The instrument may be capable of forming a torque-transmitting engagement with the shaft head separately from formation of the overall engagement between the instrument and the pedicle screw head. The instrument may have an engagement member, for engagement with an engagement feature in the driven piece that is axially translatable with respect to other parts of the instrument. The instrument may have a torque tube that is generally external of the driver tube. The instrument may be provided with an end tip with windows through which threads protrude for engagement with the internal threads of the pedicle screw head. The instrument may have a skirt for supporting the tabs against splaying while the instrument is engaged with the screw. The skirt may be part of the end tip.

In embodiments of the invention, there is provided a screw, such as a pedicle screw that has break-off tabs, suitable for use in the surgical correction of spondylolisthesis. In embodiments of the invention, there is provided an installation tool suitable for gripping the head of the screw and exerting force on the head of the screw in a direction generally along the axis of the screw head. Embodiments of the invention also provide associated surgical methods.

Embodiments of the invention can also include corresponding methods of use, and can include appropriate kits.

BRIEF DESCRIPTION OF THE ILLUSTRATIONS

Embodiments of the invention are further described in the following Figures.

FIG. 2A is a three-dimensional illustration of a pedicle screw assembly having tapered extension tabs.

FIG. 2B is the same view as that of FIG. 2A, but with the setscrew and rod omitted.

FIG. 2C is a side view of the embodiment shown in FIG. 2B.

FIG. 3B is a cross-sectional view of the pedicle screw head of FIG. 3A.

FIG. 3C is an enlargement of a portion of FIG. 3B.

FIG. 9A is a cross-sectional view of a pedicle screw of an embodiment of the invention, showing a first stage of assembly.

FIG. 9B is a similar view to that of FIG. 9A, showing a second stage of assembly.

FIG. 9C is a similar view to that of FIGS. 9A and 9B, showing a third stage of assembly.

FIG. 9D is a similar view to that of FIGS. 9A-9D, showing a fourth stage of assembly.

FIG. 13A is a three-dimensional perspective view of an engagement tip of an instrument that is an embodiment of the invention.

FIG. 13B is a three-dimensional view that is a cross-sectional view of the embodiment shown in FIG. 13A.

FIG. 14 is a three-dimensional view of an engagement tip in relation to an end tip with which it fits.

FIG. 25A is a three-dimensional view of a barrel subassembly of an embodiment of the invention.

FIG. 25B is a cross-section of the embodiment of FIG. 25A, shown along line 2B-2B.

DETAILED DESCRIPTION

Figure 1A:
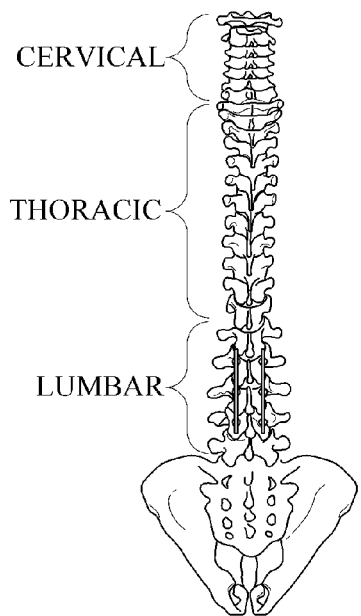
FIG. 1A is a general anatomical illustration of the spine and of typical placement of pedicle screws and spinal rods.
Figure 1B:
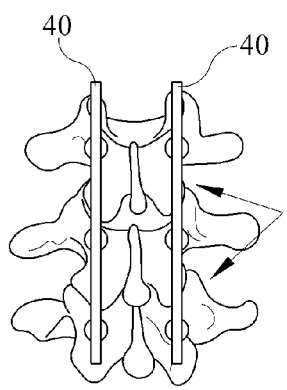
FIG. 1B is a close-up of the view of FIG. 1A.
Figure 1C:
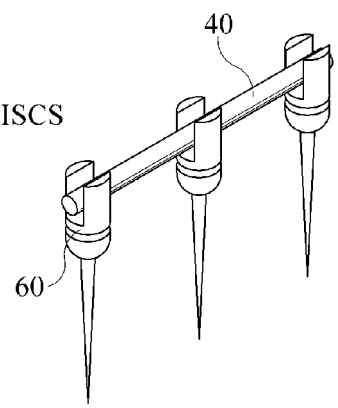
FIG. 1C is a close-up of the view of FIG. 1B, from a different perspective, illustrating use of an extended-length screw in performing reduction.
Figure 1D:
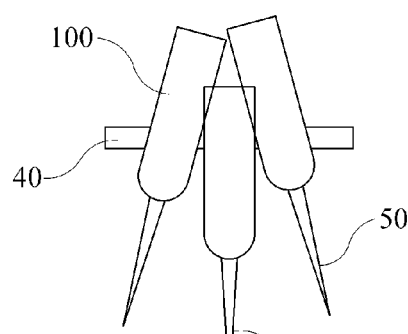
FIG. 1D is a side view of a rod and pedicle screws, illustrating interference early in a process of reduction.
Figure 1E:
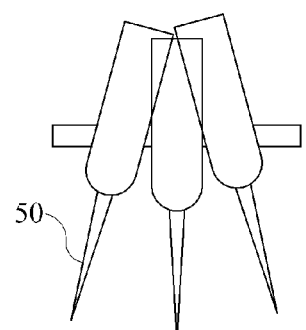
FIG. 1E is a similar view to that of FIG. 1D, illustrating interference later in the process of reduction.

For reference, FIG. 1 shows typical spinal vertebrae and typical placement of pedicle screws and spinal rods, according to the prior art. Typically, one spinal rod 40 is placed on each side of the midline of the spine (approximately the sagittal plane of the patient's body). Typical pedicle screws 50 have a head 60, which may have extension tabs 100. Pedicle screws 50 may also have a shaft 80 that may be threaded so as to engage bone. Spinal rod 40 passes through slots in the screw heads 60. FIGS. 1D and 1E illustrate that it is possible for the extension heads 100 of pedicle screws to interfere with each other. FIG. 1D illustrates such interference at the beginning of a spondylolisthesis reduction, and FIG. 1E illustrates such interference at the end of a spondylolisthesis reduction.

FIGS. 2A-2C illustrate an embodiment of the invention. In these illustrations, the pedicle screw 50 has a head 60 and a shaft 80. In embodiments of the invention, the shaft 80 may be movable with respect to the head 60 (polyaxial), as illustrated; or, alternatively, the shaft 80 may be fixed with respect to the head 60 (monoaxial).

Attached to, or integral with, the screw head 60 may be extension tabs 100a, 100b. An extension tab 100a, 100b may be located on each side of screw head 60. Extension tabs 100a, 100b may be symmetric with each other, although they do not have to be. Extension tabs 100a, 100b may be defined at least in part by a stress concentration feature or weakened region, as described elsewhere herein, which may promote a location of breaking off of the extension tabs 100a, 100b from the screw head 60. The interior of extension tabs 100a, 100b may be engageable with a setscrew 90 so as to urge spinal rod 40 and screw head 60 toward each other, particularly if there is a substantial distance over which spinal rod 40 and screw head 60 need to be brought together. Extension tabs 100a, 100b can be broken off from screw head 60 when they are no longer needed during surgery.

It is possible that screw head 60 may have on its exterior an indentation 70a, and another opposed indentation 70b on an opposite side of the screw head 60. The locations of indentations 70a, 70b may be at opposed locations on the side of the head 60, 180 degrees apart from each other. It is further possible that extension tabs 100a, 100b may also have such an indentation 102a, 102b on their exteriors. Indentations 102a, 102b in extension tabs 100a, 100b could be identical to indentations 70a, 70b in screw head 60, but they do not have to be. An indentation 70a on one side of screw head 60 could be identical to a corresponding indentation 70b on the opposed side of screw head 60, or alternatively could be different. An indentation 102a on extension tab 100a could be identical to a corresponding indentation 102b on extension tab 100b, or alternatively could be different.

Extension tabs 100*a*, 100*b* may be internally threaded with an internal thread 104*a* on extension tab 100*a* and an internal thread 104*b* on extension tab 100*b*. The internal threads 104*a*, 104*b* on extension tabs 100*a*, 100*b* and the internal thread 106 inside the permanent part of screw head 60 may all be part of a common helical thread path, so that a setscrew 90 can thread continuously along all those threads and thereby advance in a distal direction upon being rotated appropriately. However, it is not necessary for the threads 104*a*, 104*b*, 106 all to be physically continuous with each other. For example, it is possible that there could be an interruption in the internal threading at the boundary between screw head 60 and extension tabs 100*a*, 100*b*, and between extension tabs 100*a* and 100*b* there can be empty space that interrupts the threads 104*a*, 104*b*.

Referring now to FIG. 2C, at least one of extension tabs 100*a*, 100*b* may be smaller, in at least one dimension, proximally than it is distally. FIG. 2C is a side view illustrating a taper 130 such as would be created by cutting planes intersecting the screw head 60. However, other geometries such as non-straight tapers are also possible. The taper 130 may be such as to allow screw heads 60 to avoid interfering with each other in certain anatomical situations, as described elsewhere herein. It is possible that extension tabs 100*a*, 100*b* may end their taper 130 at approximately the location of stress concentration feature as described elsewhere herein, and the screw head distal of the stress concentration feature may be un-tapered. However, this is optional; it is also possible that the taper 130 could either begin or end either more proximally or more distally than described. Although a straight taper has been illustrated, other geometries such as curved are also possible.

Referring now to FIGS. 3A-3C, and 24A and 24B, a pedicle screw is shown with a geometry regarding a stress concentration feature.

The pedicle screw head 60 may have an external stress concentration feature 150 such as to help define a location for breaking off of extension tabs 100*a*, 100*b* from screw head 60. The external stress concentration feature 150 may extend around the external circumference of the pedicle screw head 60 in a substantially axisymmetric manner; wherever material exists into which external stress concentration feature 150 can be formed. The external stress concentration feature 150 may be interrupted, given that not everyplace on the circumference of screw head 60 may have material into which an external stress concentration feature 150 can be formed. External stress concentration feature 150 may be in the form of a groove. Alternatively, the stress concentration feature or weakened region may be a series or an array of holes or perforations 1192 (as shown in FIG. 24B). The surfaces of external stress concentration feature 150 may be generally smooth. It is possible, as an alternative, that external stress concentration feature 150 could in some way be non-axisymmetric.

Figure 3A:
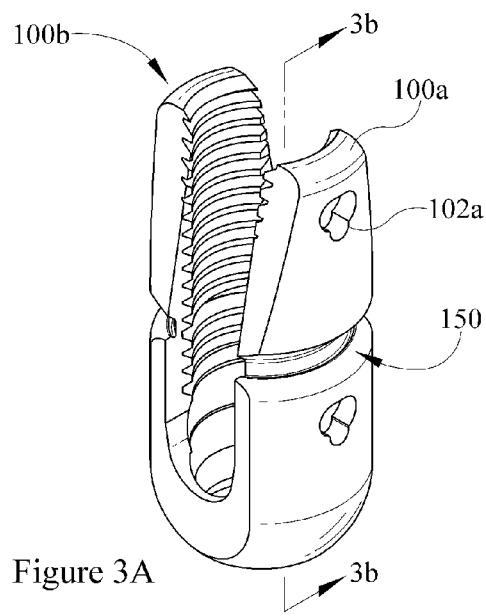
FIG. 3A shows a pedicle screw head of an embodiment of the invention, in which a pedicle screw has certain features regarding an external stress concentration feature.
Figure 3A:
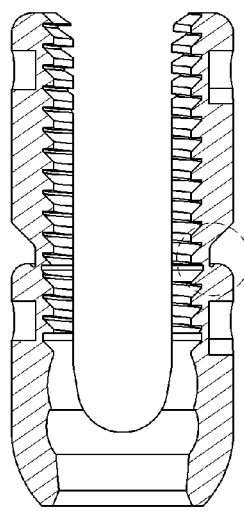
Figure 3A:
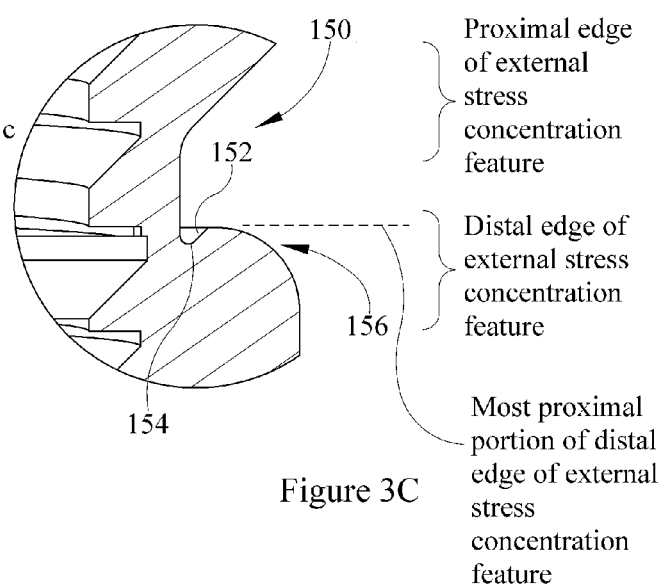

With continued reference to FIGS. 3A-3C, it is furthermore possible that the external stress concentration feature 150 may be provided with an undercut 152. The undercut 152 may have an undercut bottom 154 where the material is removed deepest in the distal direction along the axial direction of the pedicle screw head 60. The undercut bottom 154 may be more distally located than a radially-oriented portion of undercut 152, or more distally than the place 156 where the external stress concentration feature 150 meets the external surface of the pedicle screw head 60, and may be located somewhat internally within the screw head 60. The undercut 152 may be located at or near the most radially-inward portion of external stress concentration feature 150.

Figure 4A:
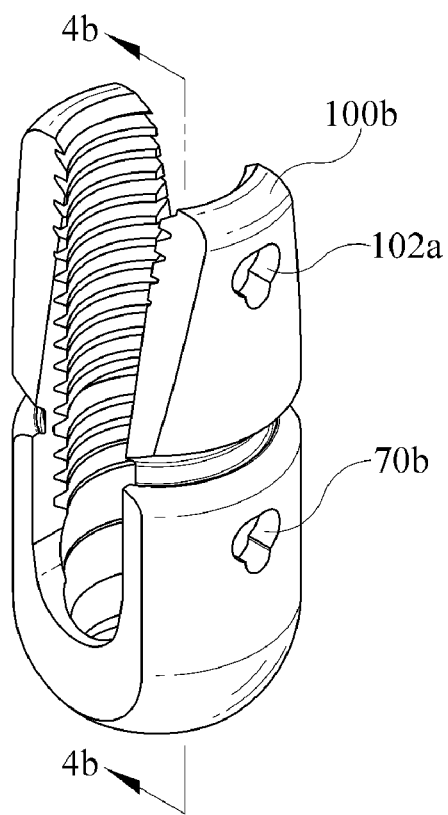
FIG. 4A shows a pedicle screw head of an embodiment of the invention, in which a pedicle screw has certain features regarding an internal stress concentration feature.
Figure 4B:
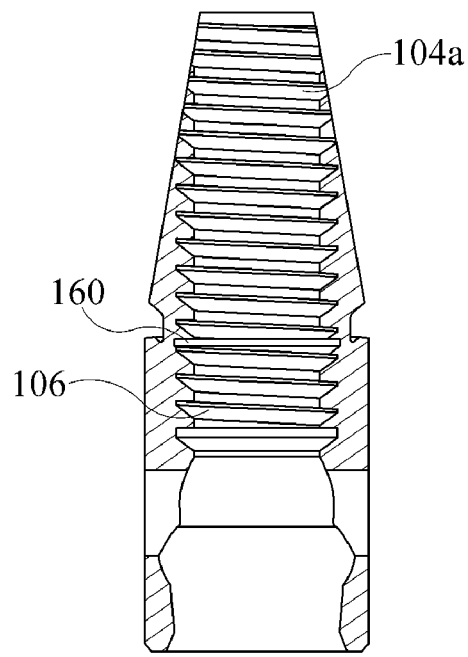
FIG. 4B is a cross-sectional view of the pedicle screw head of FIG. 4A.

Referring now to FIGS. 4A and 4B, the pedicle screw 50 may be provided with an internal stress concentration feature 160. Internal stress concentration feature 160 may project outwardly from the interior of screw head 60. It is possible that the internal stress concentration feature 160 may extend, in a substantially axisymmetric manner, wherever material exists into which the internal stress concentration feature 160 can be formed. Internal stress concentration feature 160 may be interrupted such as by the gap between extension tabs 100*a*, 100*b*. Internal stress concentration feature 160 may have the form of a groove. Alternatively, the stress concentration feature 160 may be a series or an array of holes or perforations (not shown). Internal stress concentration feature 160 may be generally axisymmetric even though it may exist in generally the same region as the helical internal thread 106, which is non-axisymmetric, and which is formed into the interior of screw head 60. If desired, internal stress concentration feature 160 may be deep enough to completely remove any vestige of internal threads 104*a*, 104*b*, 106 in the interior of the groove. Alternatively, it is possible that internal stress concentration feature 160 could have less than such a depth and could remove some but not all of the profile of threads 104*a*, 104*b*, 106. It is possible, as yet another alternative, that internal stress concentration feature 160 could in some way be non-axisymmetric.

Figure 5A:
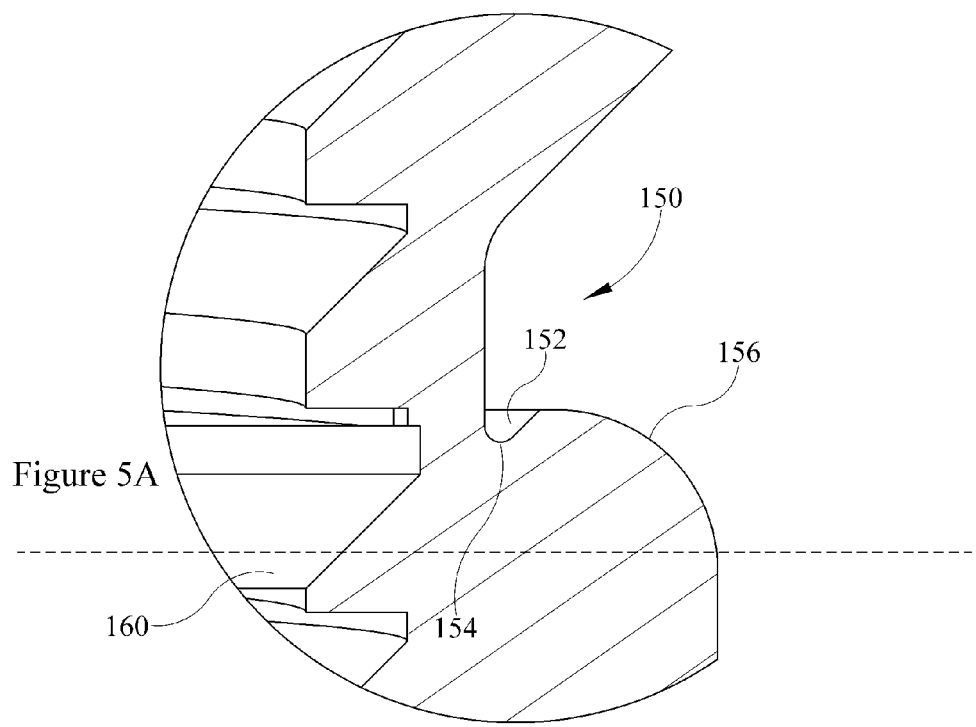
FIG. 5A illustrates an interrelationship between the external stress concentration feature and the internal stress concentration feature.

Referring now to FIG. 5A, the internal stress concentration feature 160 may have a certain defined geometric relationship with the external stress concentration feature 150. The internal stress concentration feature 160 may have an axial location and a cross-sectional geometry such that the internal stress concentration feature 160 may be located equally distally or more distally with respect to the undercut bottom 154 of the undercut 152 of external stress concentration feature 150. It is possible that a least-distal point of internal stress concentration feature 160 could be more distal than a most-distal radially-oriented plane of the profile of external stress concentration feature 150.

Figure 5B:
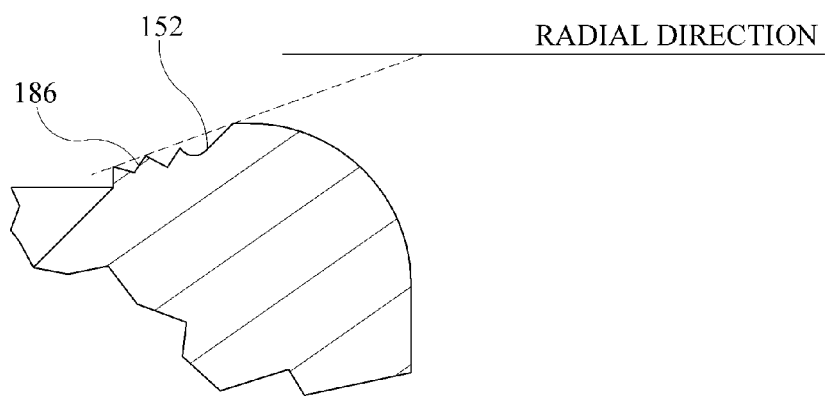
FIG. 5B is a view of a likely fracture surface for the embodiment of FIG. 5A, after removal of the extension tab from the screw head.

Referring now to FIG. 5B, The external concentration feature 150, its undercut 152, and the internal concentration feature 160 may cooperate to at least partially determine a fracture path that occurs when extension tab 100*a*, 100*b* is eventually removed from screw head 60. It is believed that in this situation, a fracture path may be approximated as the shortest path between points on the external stress concentration feature 150 (including its undercut 152) and points on the internal stress concentration feature 160, although it is not wished to be limited to this explanation. It is also realized that a fracture path may have a degree of randomness and may vary slightly among a plurality of fractured articles that have been manufactured as identically as possible. Therefore any description of a fracture path is to at least some small extent approximate. Whatever the details of the stress concentration regions 150, 160, the region may be such that if torque or lateral force is applied to the tab, bending will occur preferentially at the stress concentration region 150, 160, and will eventual fracture after sufficient or repeated torqueing or flexing of the tab.

It is envisioned that when the extension tab 100*a* or 100*b* is eventually removed from the pedicle screw head 60, the external end of the fracture surface 186 will be at or near the undercut bottom 154 of the external stress concentration feature 150, and therefore will be located more distally than a nearest surface of external stress concentration feature 150 that is intended to remain with screw head 60 after removal of extension tab 100. Thus, the fracture surface 186 may be at least somewhat recessed in relation to the nearest surface of external stress concentration feature 150 that remains after fracture. Furthermore, the path of the fracture surface 186, or of a smooth line that generally approximates the possibly rough fracture surface 186, may angle inward as illustrated in FIG. 5B.

Surfaces that are near the fracture surface 186, such as surface 156, may be substantially smooth, because for example they may be machined surfaces. In this way, bodily tissue that may contact the pedicle screw head 60, may first contact a portion of the external stress concentration feature 150 that is an as-manufactured smooth surface, before such bodily tissue reaches the possibly-rough fracture surface 186. It is even possible that bodily tissue might not ever reach the fracture surface 186 because of the recessing of the fracture surface 186 relative to other surfaces. It is believed, although it is not wished to be limited to this explanation, that this limiting or preventing of contact of bodily tissue with fracture surfaces may reduce the likelihood of bodily tissue being irritated by potentially sharp or irregular fracture surfaces 186.

In general, it is possible that an undercut configuration 152 could be provided on an external stress concentration feature 150, either together with or in the absence of an internal stress concentration feature 160. Many geometries and designs are possible for both external stress concentration feature 150 and internal stress concentration feature 160, including both axisymmetric and non-axisymmetric designs.

Figure 6:
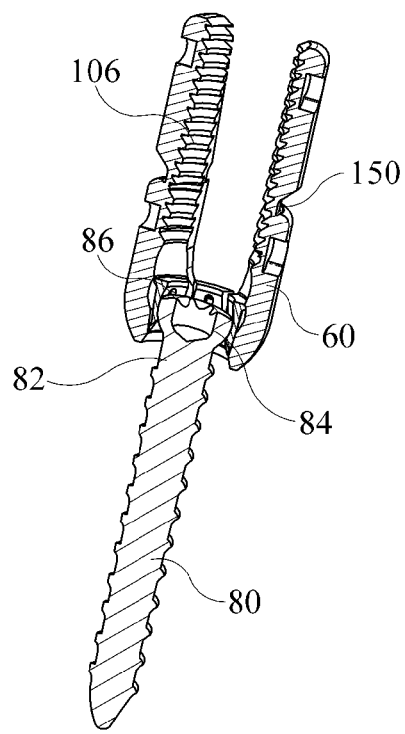
FIG. 6 is a three-dimensional sectional view of a screw of an embodiment of the invention that is a frictional polyaxial screw.

Referring now to FIG. 6, screw 50 may be a polyaxial screw in which the screw head 60 is capable of assuming a plurality of angular orientations of the screw head 60 relative to the screw shaft 80. In an embodiment of the invention, the polyaxial screw could be a frictional polyaxial screw capable of retaining, with some amount of frictional force, whatever angular orientation is established of the screw head 60 relative to the screw shaft 80. Friction may be established by use of a collet 86 interposed between a shaft head 82 connected to the screw shaft 80, and the interior of screw head 60.

Figure 7:
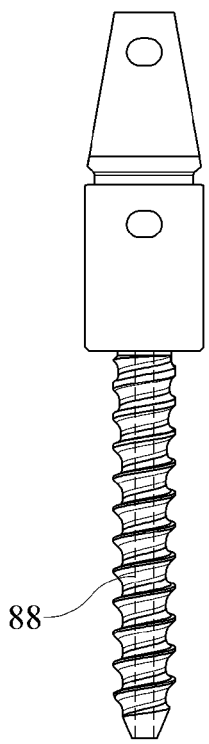
FIG. 7 is a side view of a screw of an embodiment of the invention that is a cannulated polyaxial screw.

FIG. 7 shows a screw shaft 80 having a centrally located hole 880 running the entire length of the screw shaft 80. In this embodiment, the screw shaft 80 is cannulated having a generally axially centrally located hole 88 either through the entire length of the screw shaft 80 (an open-ended hole) or through a proximal portion of the screw shaft 80 (a closed-ended hole).

Figure 8:
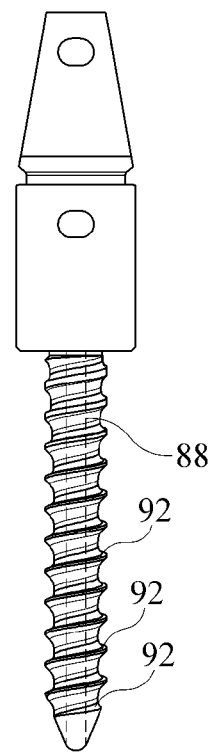
FIG. 8 is a side view of a screw of an embodiment of the invention that is a cannulated and fenestrated polyaxial screw.

FIG. 8 illustrates a screw shaft 80 with a centrally located hole 88 running most of the length of the screw shaft 80, with the centrally located hole 88 communicating with sideways holes 92. In this instance, the centrally-located hole 88 is illustrated as being a dead-end hole. If the screw shaft 80 is cannulated either partway or all the way along its length, it is further possible that the screw shaft 80 could be fenestrated, having at least one sideways hole (fenestration) 92 connecting the generally axially centrally located hole 88 with the external surface of the screw 50.

FIG. 9 illustrates a possible assembly sequence for a frictional pedicle screw assembly as has been described herein and as was illustrated in FIG. 6. FIG. 9A shows the screw head 60 and the collet 86 separately prior to assembly. The screw head 60 has an open end 62, suitable to accept a spinal rod 40 and setscrew 90, and has an opposed end 64, having a hole therethrough. In FIG. 9B, the collet 86 is located partly inside the screw head 60. This can be achieved by inserting the collet 86 through the open end 62 of the screw head 60. In FIG. 9C, the shaft 80 of the screw has been inserted into the screw assembly such that the shaft head 82 (ball shaped) at the end of the shaft 80 of the screw is captured in the interior of collet 86. This can be accomplished by inserting the shaft head 82 at the end of the shaft 80 through the opposed end 64 of the screw head 60, while the collet 86 is in the position already illustrated in FIG. 9B. FIG. 9C shows the shaft head 82 of screw shaft 80 already snapped into collet 86, with the collet 86 in the same position as it was in FIG. 9B, relative to screw head 60. In FIG. 9D, all components are shown in a final assembled position, such that both the collet 86 and the shaft head 82 at the end of the shaft 80 are moved farther toward the distal end of screw head 60 than they were in FIG. 9C. In the position shown in FIG. 9D, the collet 86 and the shaft head 82 at the end of the shaft 80 are retained in the illustrated position, and the shaft head 82 at the end of the shaft 80 is able to rotate within a defined range, with some friction being exerted on it by collet 86.

Figure 10:
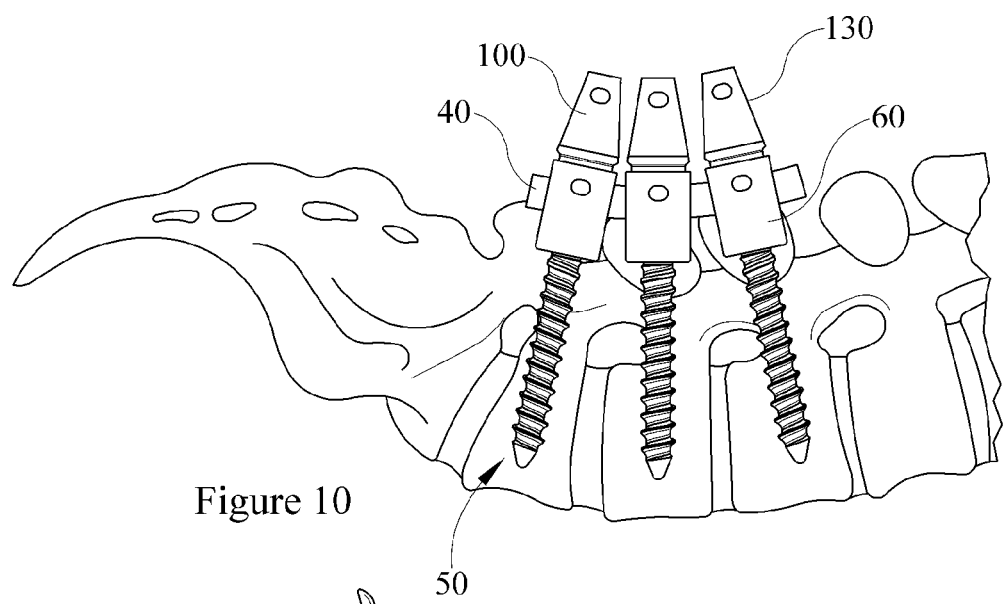
FIG. 10 is a side-view illustration showing three pedicle screws of an embodiment of the invention being used for reducing a spondylolisthesis condition.

The use of screws that are an embodiment of the invention is illustrated in FIG. 10. FIG. 10 shows three pedicle screws 50. Each screw 50 may have extension tabs 100 having a taper 130, in a lordotic situation that makes it geometrically useful to have a taper 130 as in embodiments of the invention. When such pedicle screws 50 are in use, one or more of such pedicle screws 50 could be implanted in appropriate vertebrae of a patient. Then, a spinal rod 40 could be placed in the pedicle screws 50 and could be tightened down in at least one of the pedicle screws 50. Then, in a pedicle screw 50 that has not yet been tightened but through which the spinal rod 40 passes, a setscrew 90 could be placed in the region defined by extension tabs 100a, 100b, and the setscrew 90 could be tightened enough to urge its pedicle screw head 60 and the spinal rod 40 into closer engagement with each other. FIG. 10 illustrates the situation after this has been performed.

Figure 11:
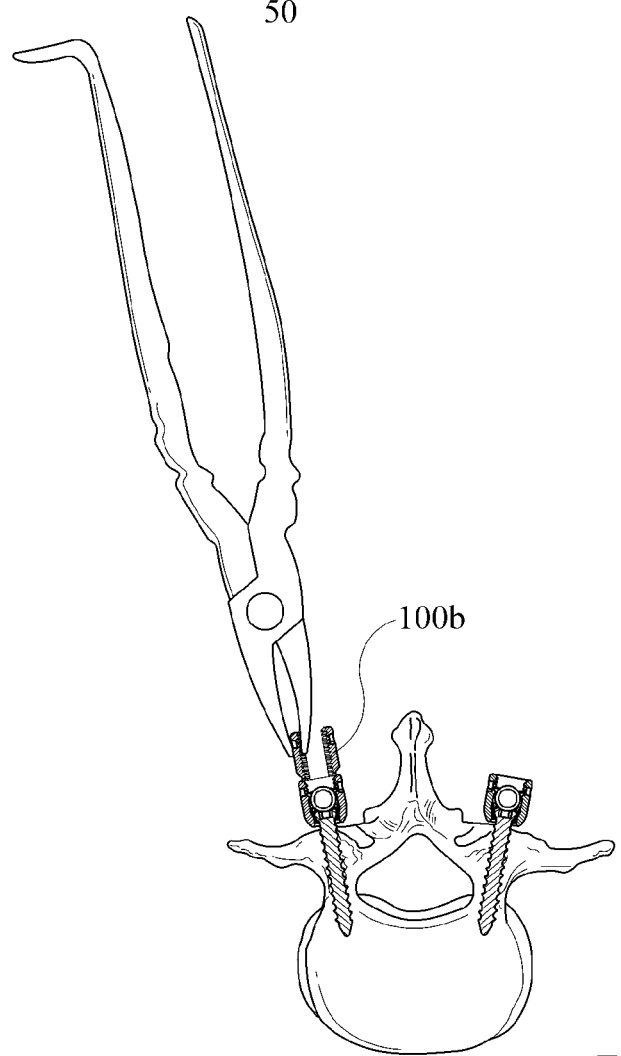
FIG. 11 is a caudal-cephalad view showing a tab being broken off from a screw of an embodiment of the invention.

Referring now to FIG. 11, a tool, such as a pair of pliers, may be used to remove the extension tabs 100a, 100b. As yet a further step, after all tightening has been performed, extension tabs 100a, 100b could be broken off from the screw head 60 to which they are connected.

The stress concentration feature may have an external stress concentration feature 150, or an internal stress concentration feature 160, or both. Many designs and geometries are possible for both external stress concentration feature 150 and internal stress concentration feature 160, including both axisymmetric and non-axisymmetric designs. Although grooves have been illustrated for the stress concentration features, still other designs of stress concentration feature are also possible, For example, a stress concentration feature could be a series or an array of holes or perforations either partly or completely through the wall of screw head 60, or could be a flat spot or series of flat spots. Any type of stress concentration feature could be used in combination with any other type of stress concentration feature. Manufacture of a stress concentration feature such as undercut 152 could be accomplished using an appropriately shaped cutting tool in a lathe. It would be possible to position internal stress concentration feature 160 more distally of external stress concentration feature 150 even in the absence of undercut 152. Even though there might be less guarantee of recessing of fracture surface 186 than there would be in the presence of undercut 152, there still could be some benefit in terms of orienting the fracture surface so that it is less exposed to bodily tissue than would otherwise be the case. Removal of extension tabs 100 from screw body 60 has been described herein using words such as break or fracture, but it should be understood that any suitable method of removal of extension tabs 100 is also contemplated. For example, a cutting operation could be possible, and what is referred to herein as a fracture surface could be a cut surface. It would also be possible to use combinations of more than one method of removing the tabs. It would also be possible to perform a smoothing operation on the fracture surface following fracture.

Figure 12A:
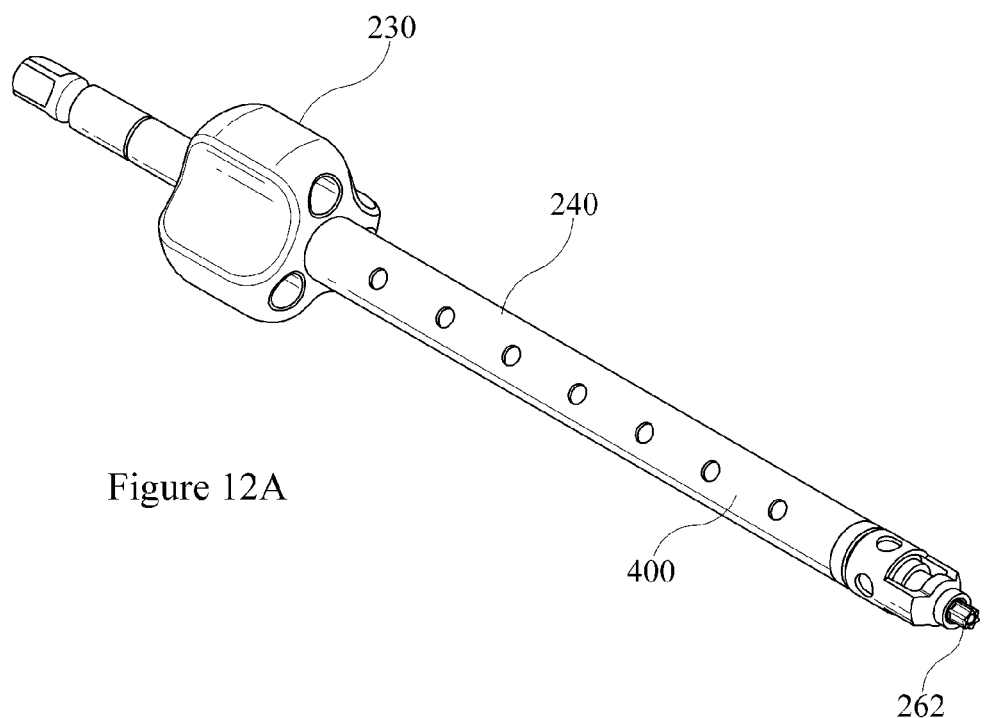
FIG. 12A is a three-dimensional perspective view of an instrument that is an embodiment of the invention.
Figure 12B:
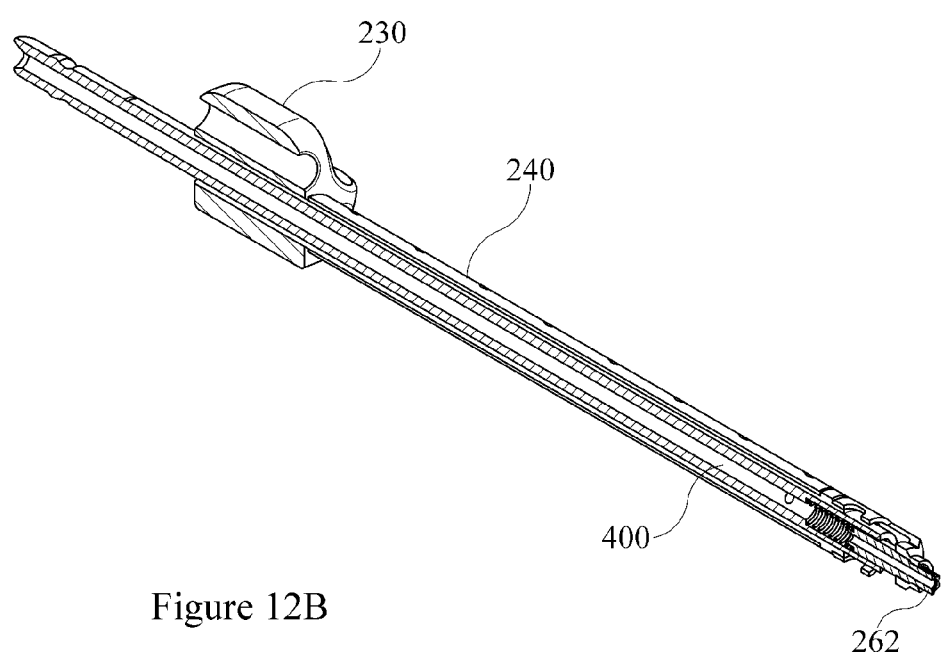
FIG. 12B is a three-dimensional view that is a cross-sectional view of the embodiment shown in FIG. 12A.

Additional embodiments of the invention provide an instrument for driving screws. The instrument could be used to drive the break-away screws described herein, or more generally could be used to drive any screw as may be desired. First, an embodiment of such an instrument is illustrated in FIG. 12A in full and in FIG. 12B in cross-section.

The instrument may be suitable to engage a screw such as a polyaxial pedicle screw. Typically a polyaxial pedicle screw may be provided with a screw head 60 and a screw shaft 80, with the screw shaft 80 having a shaft head 82 located at least partially inside the screw head 60. Typically the shaft 80 may be able to angulate within a limited angular range with respect to the screw head 60, and the shaft 80 may also be able to spin around the axis of the shaft 80, with possibly an unlimited range of spinning. Typically the polyaxial screw head 60 may have an internal thread 106, such as for engaging a setscrew to hold a spinal rod 40 in place. In addition, the shaft head 82 may have an engagement feature 84 for engagement with a driving tool. The geometry of engagement feature 84 may be female, and may for example be a hex socket, or a Torx® geometry, or a hexalobe geometry, or other suitable geometry.

The instrument, when assembled to a pedicle screw, may have two types of contact with the screw. A portion of the instrument may engage the internal threads 106 of the screw head 60 or internal threads 104a, 104b of tabs 100a, 100b for purposes of attaching the instrument to the polyaxial screw during the installation process. This may be referred to as the drive system. Another portion of the instrument may engage the engagement feature 84 in shaft head 82 for purposes of transmitting torque to the engagement feature 84 in the shaft head 82. This may be referred to as the torque system.

In general, and as will be apparent from description elsewhere herein when the instrument is fully engaged with a polyaxial screw, i.e., with the engagement tip 262 engaging with the engagement feature 84 and the threaded tip 320 engaging with the internal threads of screw head 60 or tabs 100a, 100b, it might be possible for the threaded tip to transmit some torque to the screw head that might in turn transmit some torque to screw shaft 80, depending on details of the relationship between screw head 60 and screw shaft 80. However, the instrument may be used such that torque is applied by the user primarily to the torque shaft 240 for transmission to shaft head 82 and thereafter to shaft 80. The screw shaft 80 may thereby advance into bone upon being rotated. It is possible that when the instrument is engaged with screw head 60 and engagement tip 262 is engaged with engagement feature 84, there may be a constrained angular orientation of screw head 60 relative to screw shaft 80, such as with the axis of screw shaft 80 being coincident with an axis of symmetry of screw head 60. However, when the instrument is removed from the polyaxial screw, such a constraint may no longer exist and various angular orientations of screw head 60 with respect to screw shaft 80 may be possible.

Referring now to FIG. 13, there is illustrated an engagement tip 262 of the instrument. The distal end of engagement tip 262 may have a non-circular prismatic (sometimes termed extruded) geometry suitable to engage a corresponding feature 82 in the shaft head 82. For example, this geometry may have a hexalobe cross-section such as the commercially available Torx® geometry. The engagement tip 262 may also have other portions more proximally located that may be generally cylindrical or of any other desired shape. The engagement tip 262 may also have a central axially-oriented hole 269 therethrough that may be sized to permit passage therethrough of a guide wire or Kirschner wire (not illustrated).

Referring now to FIG. 14, the instrument may also be provided with an end tip 280 whose distal end may have a hole 282 therethrough having cross-section suitable to engage with the non-circular shape of the distal end of the engagement tip 262. As illustrated, the hole 282 is also of a hexalobe shape just slightly larger than the dimensions of the corresponding shape of engagement tip 262. As such, engagement tip 262 may be capable of translating axially with respect to end tip 280, yet torque may be transmitted from end tip 280 to engagement tip 262. FIG. 14 illustrates engagement tip 262 about to enter end tip 280 from a proximal direction such as for assembly purposes. End tip 280 may have windows 286 as further described elsewhere herein.

Figure 15:
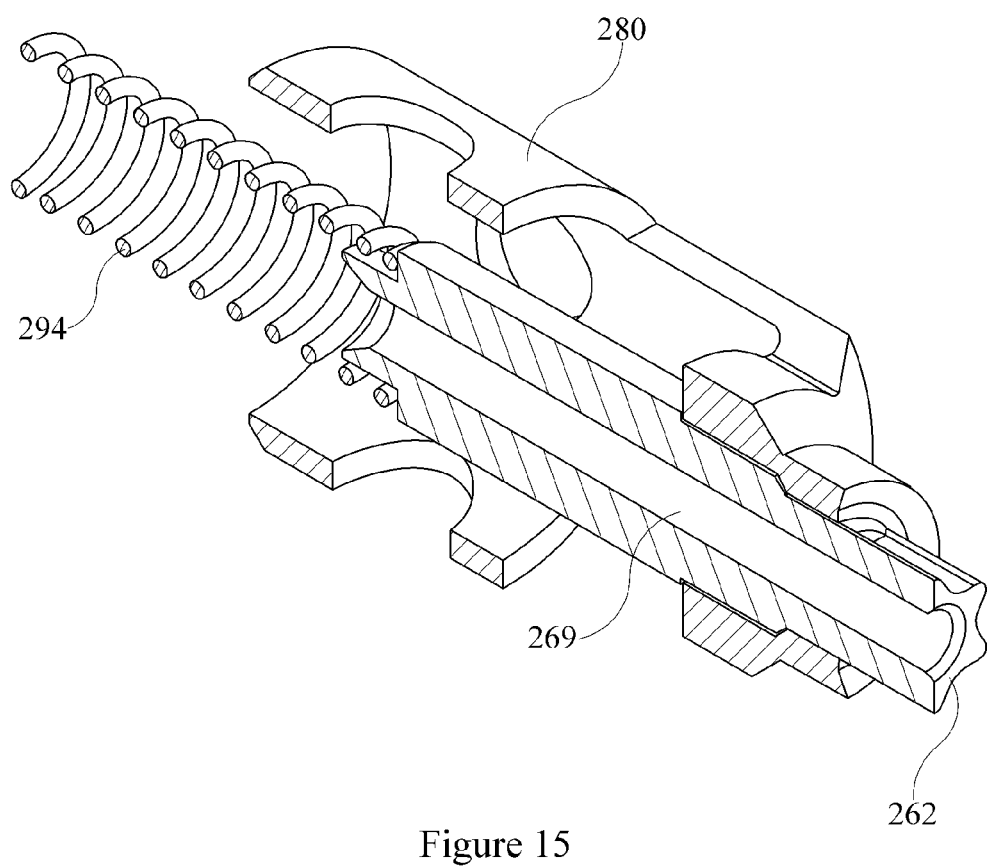
FIG. 15 is a three-dimensional sectional view of an engagement tip, an end tip and a spring.

FIG. 15 is a three-dimensional sectional view of an engagement tip 262, an end tip 280 and a spring 294. In this illustration, the engagement tip 262 is advanced as far distally as the instrument design permits. There is also illustrated spring 294 that may be suitable to urge engagement tip 262 in a distal direction.

Figure 16A:
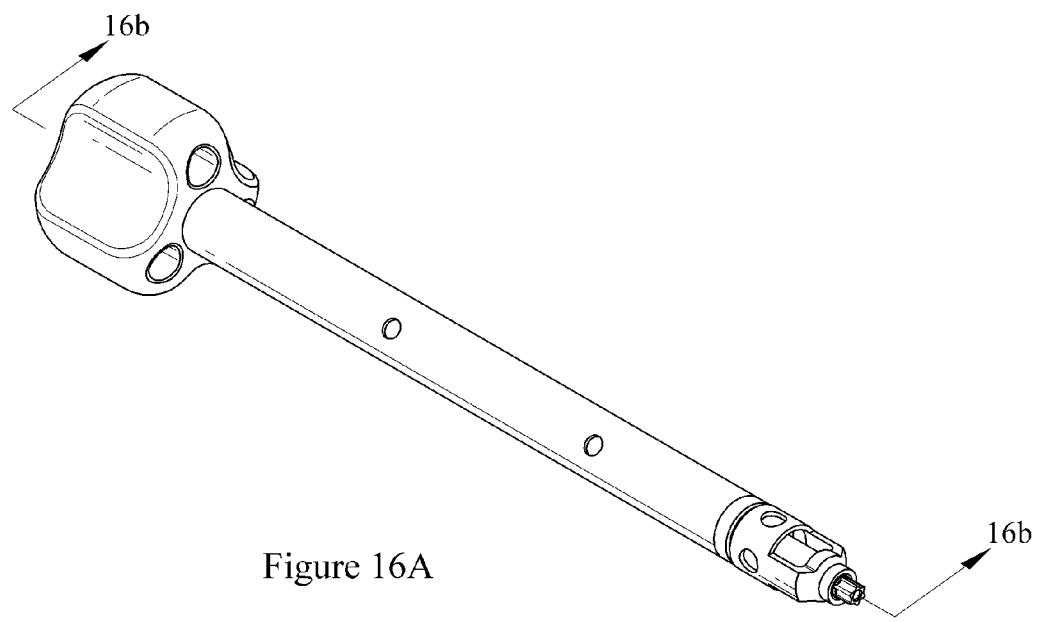
FIG. 16A is a three-dimensional view of components that cooperate to deliver torque to the shaft head, namely engagement tip, end tip, torque tube and torque handle.
Figure 16B:
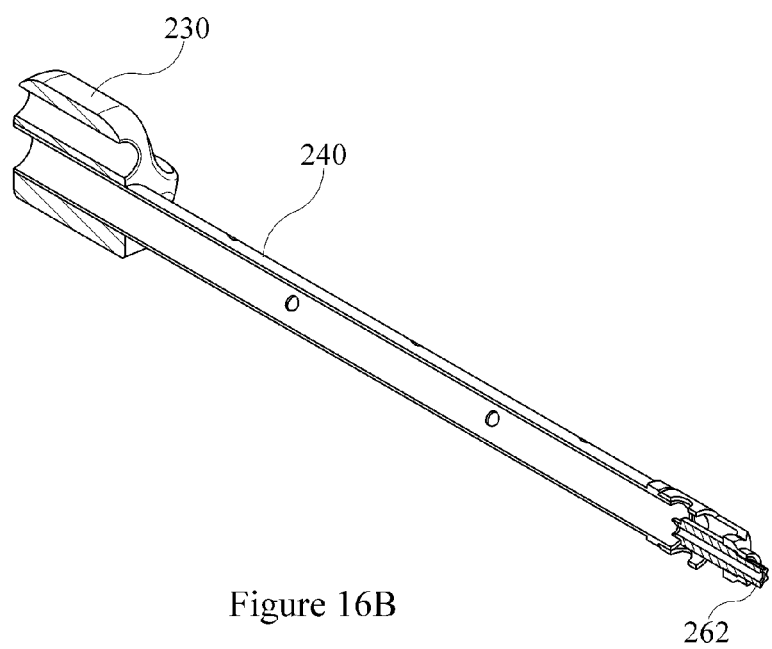
FIG. 16B is a sectional view of the components shown in FIG. 16A.

FIGS. 16A and 16B are assembly views of the components involved in transmission of torque to the shaft head. There is illustrated the engagement tip 262, the end tip 280, the torque tube 40 and the knob 230. The torque tube 240 may be rigidly attached to end tip 280, and knob 230 may be rigidly attached to torque tube 240.

Figure 17:
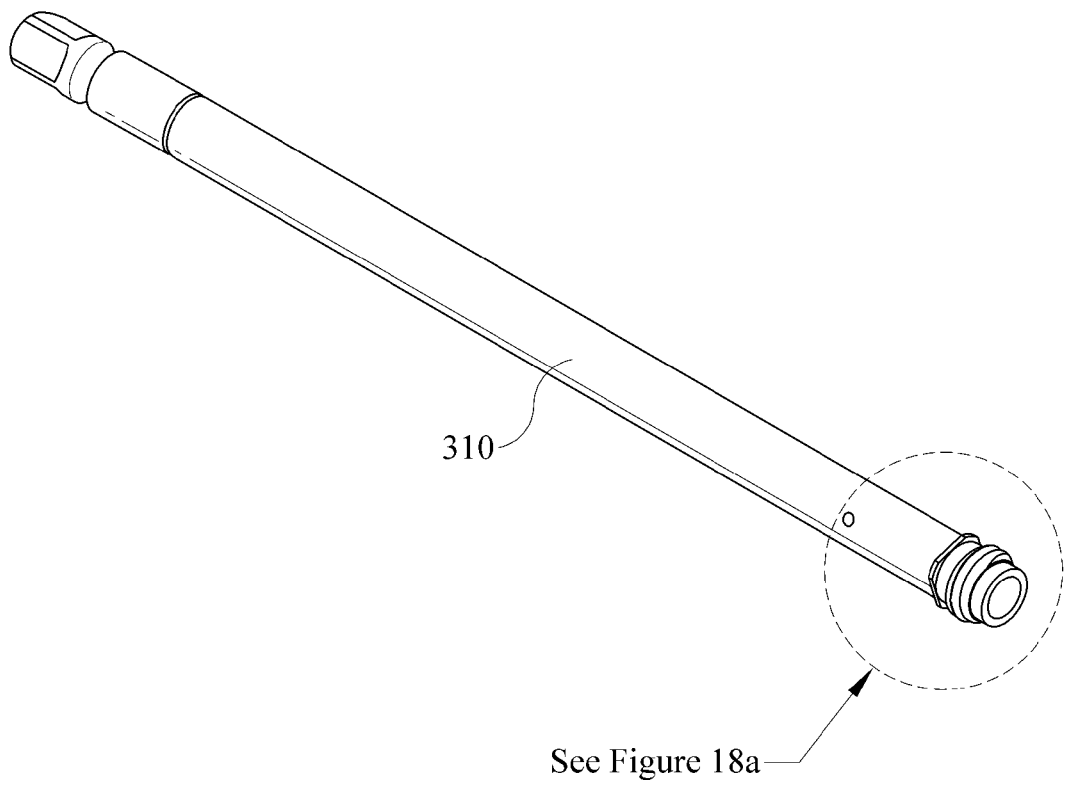
FIG. 17 is a three-dimensional view of a drive tube.
Figure 18A:
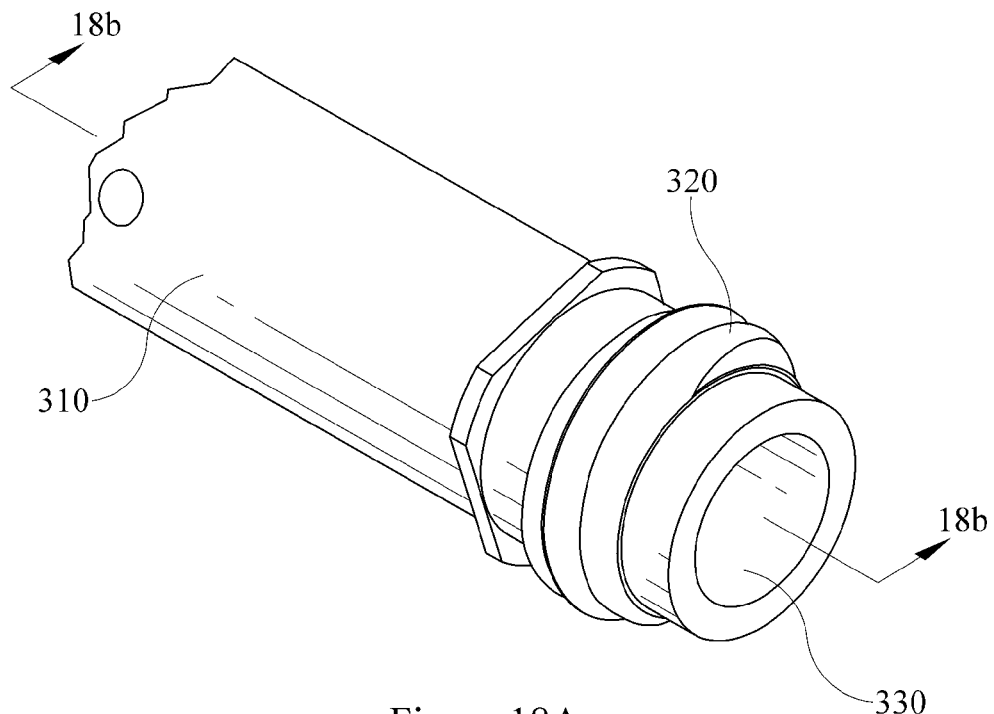
FIG. 18A is an enlargement of the distal end of the embodiment of FIG. 17.
Figure 18B:
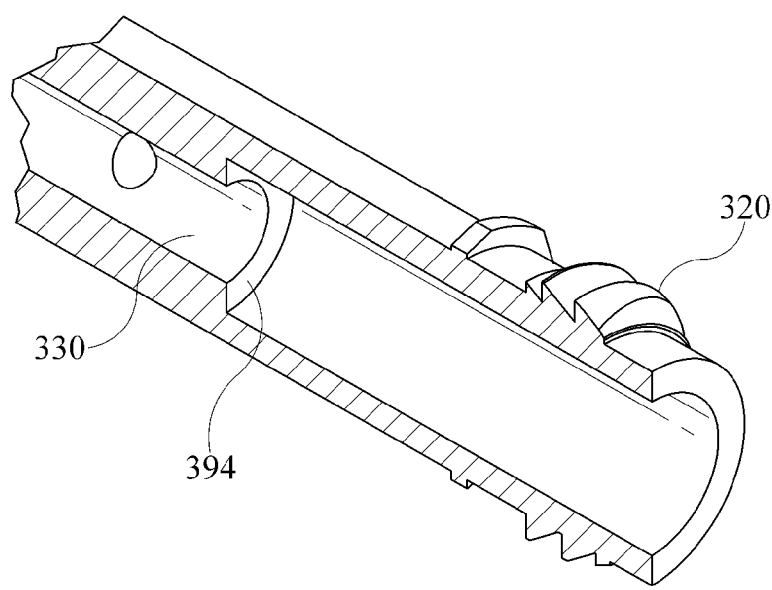
FIG. 18B is a cross-sectional view of the embodiment of FIG. 18A.

Referring now to FIGS. 17-18B, another component or set of components of the instrument, not directly involved in delivering torque to shaft head, is drive tube 310. At its distal end, drive tube 310 may have a threaded end 320, the threads being suitable to engage the either or both of internal threads 106 in the head 60 of a polyaxial screw or internal threads 104a, 104b in tabs 100a, 100b. At its proximal end, drive tube 310 may be provided with a handle or knob (not illustrated) attached to the proximal end thereof or may have a feature suitable to fit with a handle or knob (not illustrated). Drive tube 310 may be hollow, having a lengthwise hole 330. Drive tube 310 may further have an internal shoulder 394 suitable for one end of spring 294 to bear against.

As a result of various design features described herein, it is possible for the threaded tip 320 of drive tube 310 to engage the internal threads of screw head 60 or of tabs 100a, 100b and thereby mate the instrument to the pedicle screw assembly. Threads 320 may protrude through windows 286, in order to reach and engage the corresponding internal threads in the head 60 or tabs 100a, 100b of the polyaxial screw. This engagement of the threads may be accomplished regardless of whether engagement tip 262 is or is not mated with engagement feature 84 of shaft head 82. If the engagement tip 262 is also engaged with engagement feature 84 of shaft head 82, then the instrument is capable of delivering torque to shaft head 82 for purposes of driving shaft 80 into bone. If engagement tip 262 is not engaged with engagement feature 84 of shaft head 82, then it is possible to rotate end tip 280 around its longitudinal axis of rotation until an appropriate rotational position is reached, which will also rotate screw head with respect to shaft head 82. When the appropriate angular position is reached, spring 294 will urge engagement tip 262 to translate and enter into engagement with engagement feature 84 of shaft head 82. Subsequent to that occurrence, torque will be delivered to shaft head 82 to drive the shaft 80 into bone, and screw head 60 will also rotate concurrently with rotation of shaft 80.

It can be understood that for much of the length of the body of the instrument, the torque tube 240 is exterior of the drive tube 310. However, the end tip 280 is such that torque from the torque tube 240 and knob 230, which are relatively exteriorly-located, ends up being transmitted to the engagement feature 84 of the shaft head 80, which is a relatively interiorly-located feature. At the same time, external threads 320, which are part of the more interiorly-located drive tube 310, end up engaging the internal threads of the screw head 60, which are located at a more radially-outward position than the engagement feature 84 of shaft head 82. This arrangement is achieved because external threads 320 of the drive tube 310 protrude out through the windows 286 or cutouts in the end tip 280. Torque from the proximal, larger-diameter portion of the end tip 280 is carried interiorly by the two arms 284A, 284B that occupy the slots of screw head 60 that upon completion of surgery will be occupied by spinal rod 40, and such torque is further transmitted through inter-engagement of hole 282 with engagement tip 262. Engagement tip 262 is translatable with respect to end tip 280, which allows engagement tip 262 to be either engaged with engagement feature 84 or not engaged, depending on whether the relative angular positions are appropriate.

Figure 19:
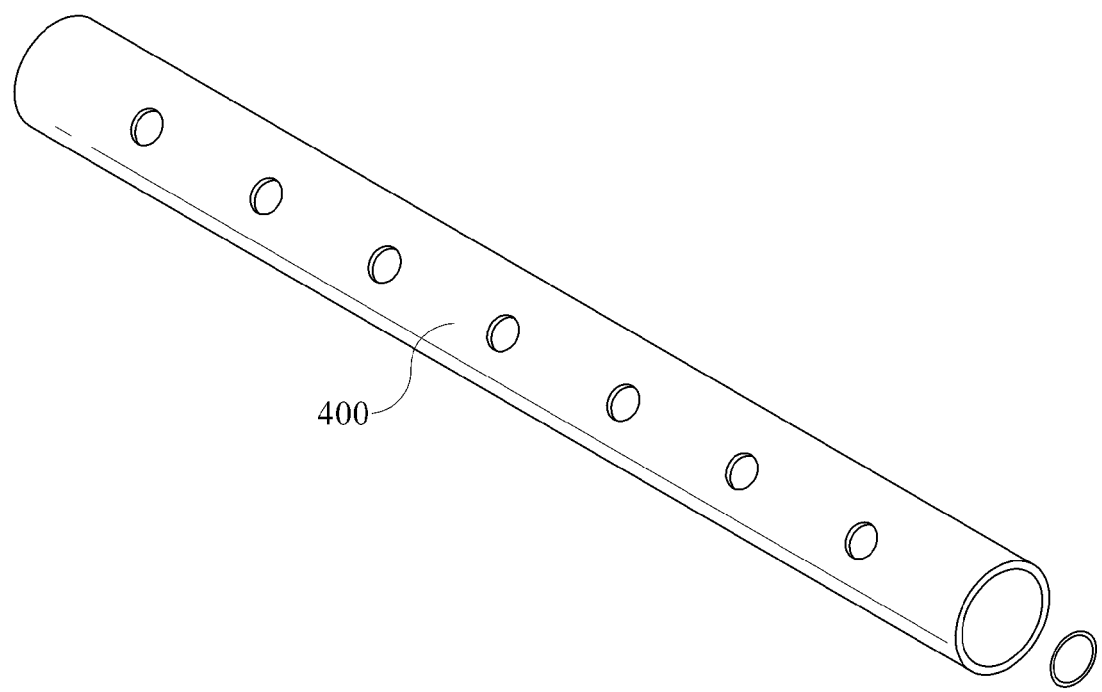
FIG. 19 is a three-dimensional illustration of the outer sleeve.

Referring now to FIG. 19, the instrument may further be provided with a loose external sleeve 400 that may be grasped by the user if desired. External sleeve 400 may be captured in its illustrated position as illustrated in FIG. 12, but may be free of any rigid connection to any other parts of the instrument. External sleeve 400 may be grasped by the user.

What has been illustrated in FIGS. 12 through 19 is an instrument that could be used with generally any polyaxial screw.

FIGS. 20-23 illustrate more specifically an instrument, which is an embodiment of the invention, for use with a polyaxial screw having break-away tabs. FIG. 20A and FIG. 20B illustrate a portion of such an instrument assembled to a polyaxial screw that has break-away tabs 100a, 100b. In this illustration, the break-away tabs 100a, 100b are tapered as described elsewhere herein.

Figure 20A:
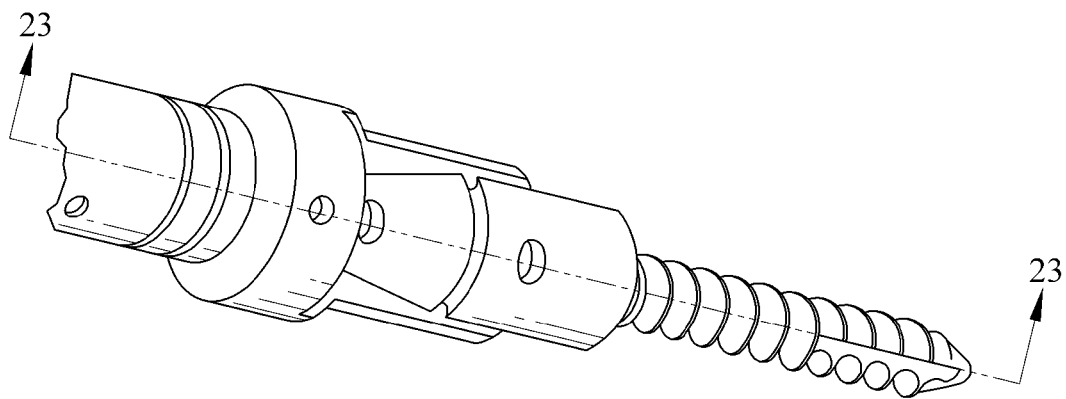
FIG. 20A is a three-dimensional view, from a first perspective, of an end tip having a skirt, and interacts with a pedicle screw having break-away tabs.
Figure 20B:
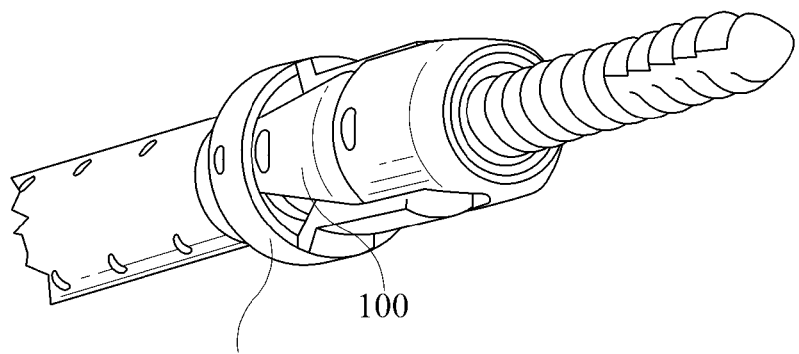
FIG. 20B is another view of the same components shown in FIG. 20A, from a second perspective.
Figure 21:
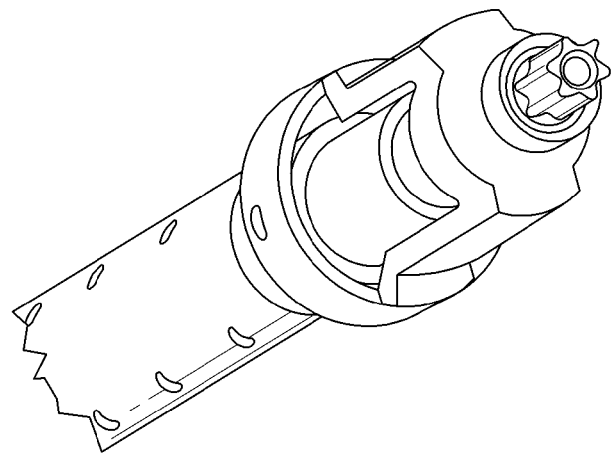
FIG. 21 is a three-dimensional view similar to the view of FIG. 20B, but shown without the pedicle screw in place.
Figure 22:
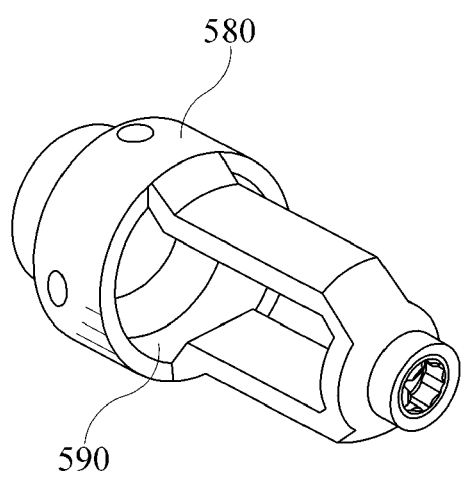
FIG. 22 is a three-dimensional view of an end tip having a skirt and long enough for use with a pedicle screw having break-away tabs.
Figure 23:
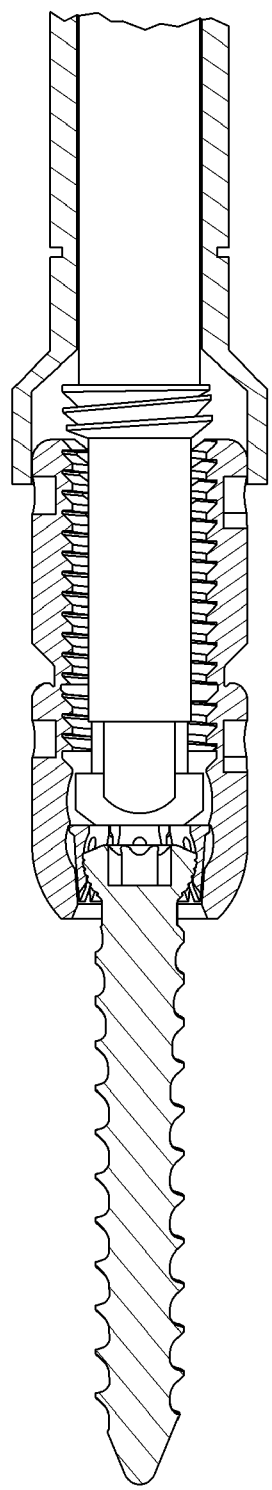
FIG. 23 is a cross-section of a distal region of the embodiment of FIG. 20A.

The instrument illustrated in FIGS. 20A-23 is generally similar to the instrument illustrated in FIGS. 12 through 19, but has a different end tip 580. If the instrument is to be used with a screw having break-away tabs 100 a, 100b, the instrument may have an end tip 580 that is appropriate for the dimensions of a screw having break-away tabs. For example, the end tip 580 may generally be longer than an end tip 280 for an ordinary polyaxial screw, as best illustrated in FIGS. 21 and 22.

Another possibility is that the end tip 580 may have a skirt 590, as best illustrated in FIGS. 20B, 21 and 22. This may be appropriate for the situation of use with a screw having break-away tabs 100, in which situation while the instrument is attached to the screw or when forces are being exerted on the instrument or the screw, there may be forces tending to splay the tabs 100a, 100b away from each other. Accordingly, the end tip 580 may have a distal end that engages with a portion of the screw head 60, and may have a proximal end that extends out to a radial dimension larger than the outer radius of the tabs 100 attached to screw head 60. Furthermore, the portion of end tip 580 that extends out to the described radial dimension may then curl back and again extend distally to form a skirt 590. The skirt 590 may have an inside diameter that is approximately equal to or slightly greater than an outside diameter of the tabs 100. More generally, the skirt 590 may be such that it either snugly or loosely fits over tabs 100. The skirt 590 may be fully axisymmetric in a complete circle, or may be interrupted so as to occupy less than a full circle. As illustrated herein, the skirt 590 is uninterrupted and is of a circular configuration. It is possible that portions of the skirt 590 may be some shape other than circular. It is possible that the skirt 590 portion may have an axial extent that is only a small portion of the length of tabs 100. The skirt 590 may be sufficiently rigid so that if tabs 100 deflect radially outward by some distance, the skirt 590 may provide some support to the tabs 100 so as to prevent or reduce further deformation by the tabs 100. Such deflection of tabs 100 could occur due to forces exerted on the tabs 100 during use of the instrument, or for any other reason.

The instrument may have a skirt 590 either with or without any other features disclosed herein, in any combination. Of course what has been described as a skirt might also be thought of as indentations in an overhanging portion of end tip 580. Such indentations could be localized to the dimensions needed to engage tabs 100a, 100b.

Referring now to the instrument as a whole, any or all of the components located on the central axis of the instrument may be cannulated so as to permit the instrument to be used with a guide wire such as a Kirschner wire. For example, engagement tip 262 is illustrated having a central hole 269 therethrough, and drive tube 310 is illustrated as being hollow, and any handle or knob that occupies the central axis could similarly be hollow.

It would also be possible that an instrument having a skirt 590 could be used with ordinary pedicle screws not having break-away tabs, or in still other situations.

Another embodiment of the invention provides a method of use of the described instrument. The instrument may be brought near and loosely engaged with a spinal screw, possibly while the screw is still in a tray or caddy, possibly without even handling the screw individually. As part of this engagement, the drive system may be operated to engage its external threads 320 with the internal threads in the screw head 60 and thereby join the instrument with the screw. At this point, it is not necessary to pay any attention to whether engagement tip 262 engages engagement feature 84 in shaft head 82. Then, the combination of the instrument and the screw may be used in surgery to implant the screw in a patient.

If the engagement tip 262 is not already engaged with the engagement feature 84 in the shaft head 82, then the first time the torque tube 240 is torqued, it will cause the engagement tip 262 to rotate with respect to the engagement feature 84 in shaft head 82 while also causing screw head 60 to rotate with respect to shaft head 82 until engagement tip 262 reaches proper angular alignment with engagement feature 84 at which time engagement tip 262 as urged by spring 294 advances into engagement with engagement feature 84. Alternatively, if desired, before the screw and instrument combination is rotated during actual implantation, the torque tube 240 can be rotated relative to the rest of the instrument or relative to the screw until the engagement tip 262 reaches proper angular alignment with engagement feature 84 and advances into the engagement feature 84 in shaft head 82.

It is possible that a kit may be supplied to surgeons. The kit may provide a variety of pedicle screws possibly of differing sizes, and spinal rods possibly of varying geometry, and setscrews and any other needed components. Appropriate tools could also be supplied. Embodiments of the invention could be provided unassembled or in partially-assembled subassemblies.

It would also be possible to use any of the described features of break-away extension tabs (100) with a monoaxial screw instead of a polyaxial screw. Although FIG. 20 illustrates an instrument holding a screw whose extension tabs (100) are tapered, such an instrument could also hold a screw whose extension tabs are not tapered, as discussed below. It would be possible for a screw to have either an undercut configuration stress concentration feature, or tapered extension tabs, or both, in any combination. Any such combination could be used either with or without a central hole (88), or with or without a frictional collet (86).

Although extension tabs 100a, 100b have been disclosed for use on the head of a pedicle screw that grasps a rod such as a spinal rod that is not the only possible use. Any of the described extension tab designs could also be used on generally any component that is involved in grasping a rod, regardless of what the distal portion of the component is like. For example, the distal portion of the component could have a hook suitable to grasp a portion of a pedicle or a lamina or a transverse process or a spinous process or in general any other anatomical feature. Similarly, any of the described extension tab designs could be used on a stud which is engaged with a plate or other structure and is suitable to grasp a rod.

Figure 24A:
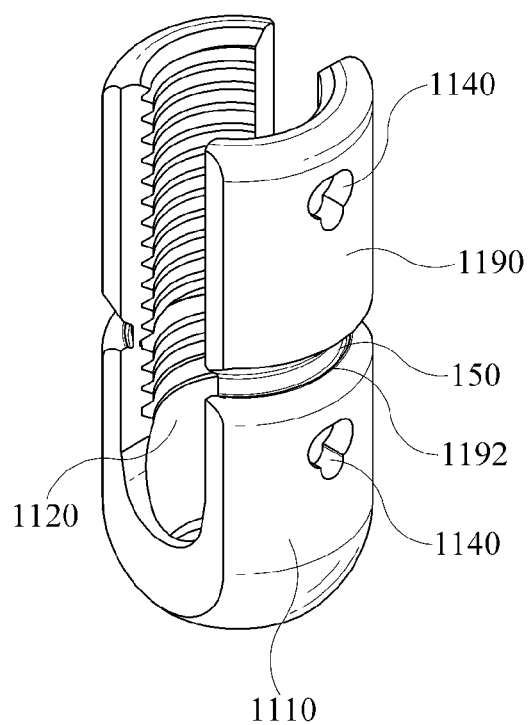
FIG. 24A is a three-dimensional perspective view of a screw of an embodiment of the invention, in which a groove provides a weak region for break-off.
Figure 24B:
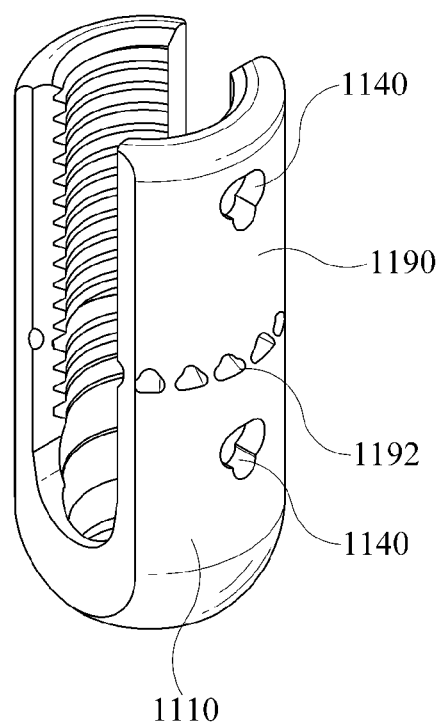
FIG. 24B is similar to FIG. 24A, except for the use of a series of perforations instead of a groove.
Figure 25C:
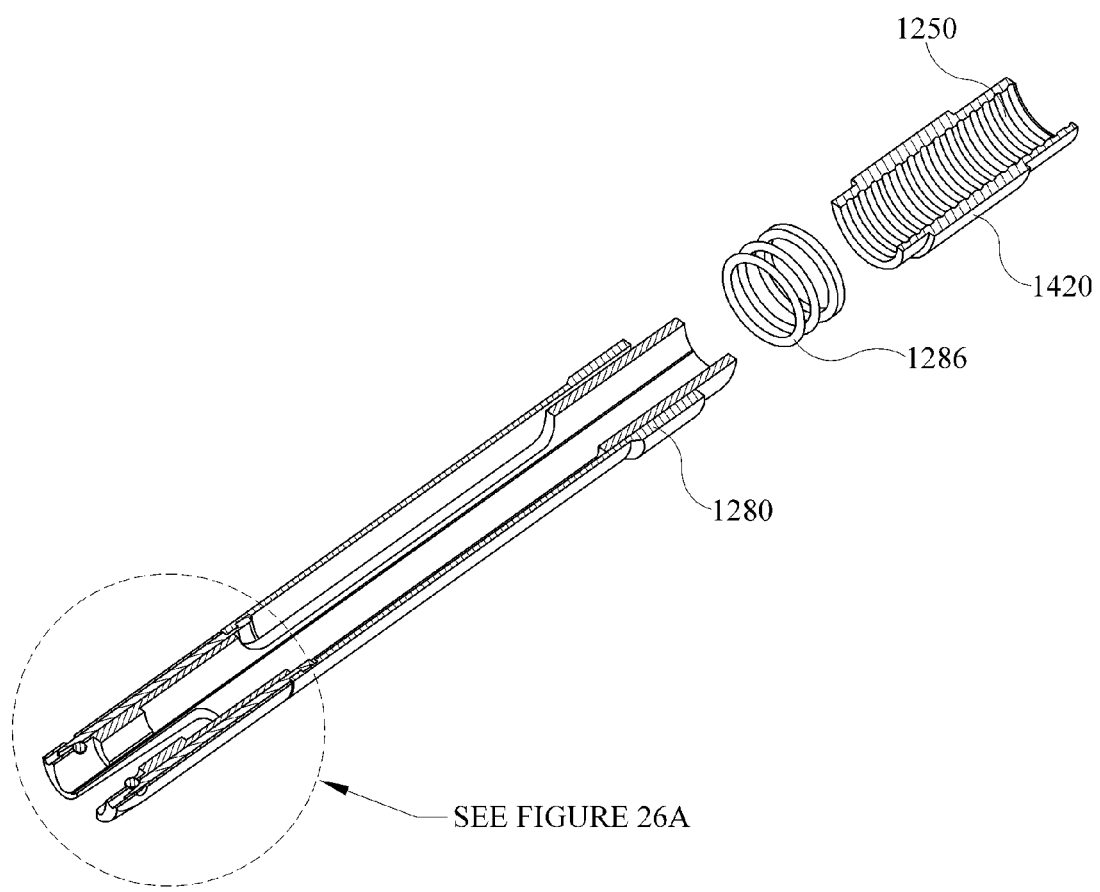
FIG. 25C is an exploded assembly view of the embodiment shown in FIG. 2B.

Referring now to FIGS. 24A and 24B, a screw 1100 may be either polyaxial or monoaxial, and may be a pedicle screw. The head 1110 of the screw 1100 may be provided with a slot 1120 therethrough, suitable to be occupied by a spinal rod 1130. The head 1110 of the screw 1100 may further be provided with a pair of indentations 140 on an external surface of the screw head 1110. The indentations 1140 may be located 180 degrees apart from each other on the periphery of the screw head 1110. The indentations 1140 may be located 90 degrees away from the general longitudinal direction of the slot 1120, and the spinal rod 1130 that may eventually occupy the slot 1120. The screw 1100 may further be provided with extended tabs 1190 that extend from the head 1110 of the pedicle screw. The tabs 1190 may be defined by a weakened or recessed region 1192 where the tabs 1190 meet the screw head 1110. A weak or weakened region is a regions that may be substantially weaker than the immediately surrounding regions. FIG. 24A illustrates a groove forming a weakened region 1192. Alternatively, as illustrated in FIG. 24B, there may be a series or an array of holes or perforations forming the weakened region 1192. Whatever the details of the recessed region 1192, the region 1192 may be such that if torque or lateral force is applied to tab 1190, bending will occur preferentially at the recessed region 1192, and will eventual fracture after sufficient or repeated torqueing or flexing of tab 190. The tabs 1190 may share an internal thread with head 1110 of the screw 1100.

Referring to FIGS. 25A-29B, an embodiment of the invention may have an installation instrument that may be provided with a barrel subassembly 1200 and a drive subassembly 1300.

Referring now to FIGS. 25A-26B, the barrel subassembly 1200 may be hollow and tubular having a longitudinal direction. The hollow bore of the barrel subassembly 1200 may be suitable for the drive subassembly 1300 to fit inside the barrel subassembly 1200.

The barrel subassembly 1200 may have a proximal end 1200p and a distal end 1200d. The barrel subassembly 1200 may have a tube 1210. The tube barrel 1210 may have, at its distal end, a slot 1220 having a lateral width that is greater than the diameter of a spinal rod 1130. The slot 1220 may have a length, along the longitudinal direction of the barrel subassembly 1200, such as to allow a spinal rod 1130 to enter the slot sufficiently far to accommodate the greatest expected offset distance of spondylolisthesis or out-of-position distance of vertebrae.

Figure 26A:
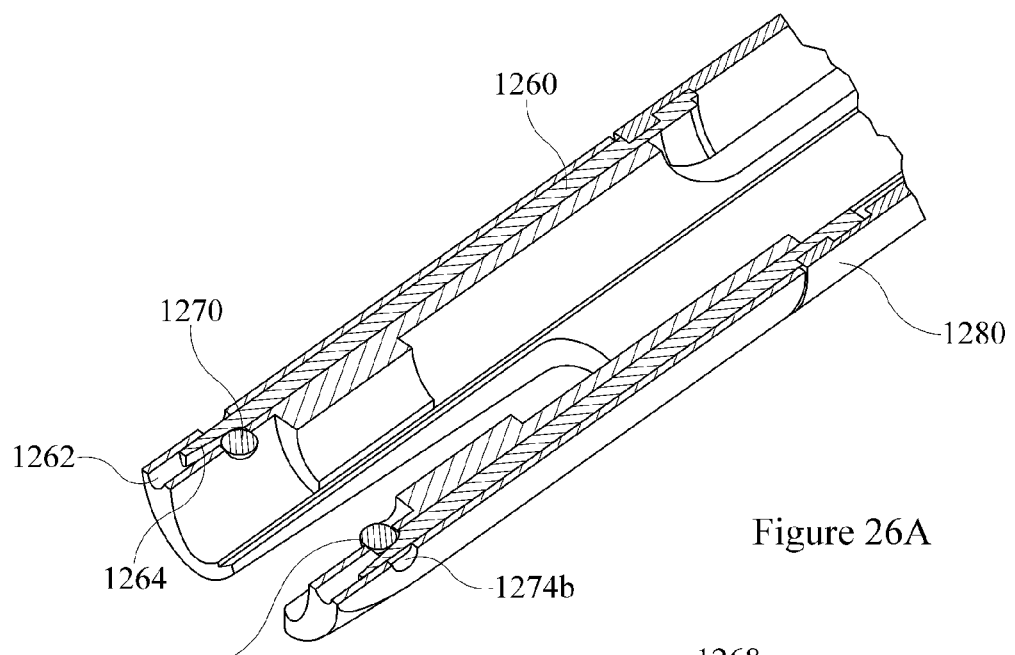
FIG. 26A is a close-up view of the embodiment shown in FIG. 25C with the long pins in an extended position.
Figure 26B:
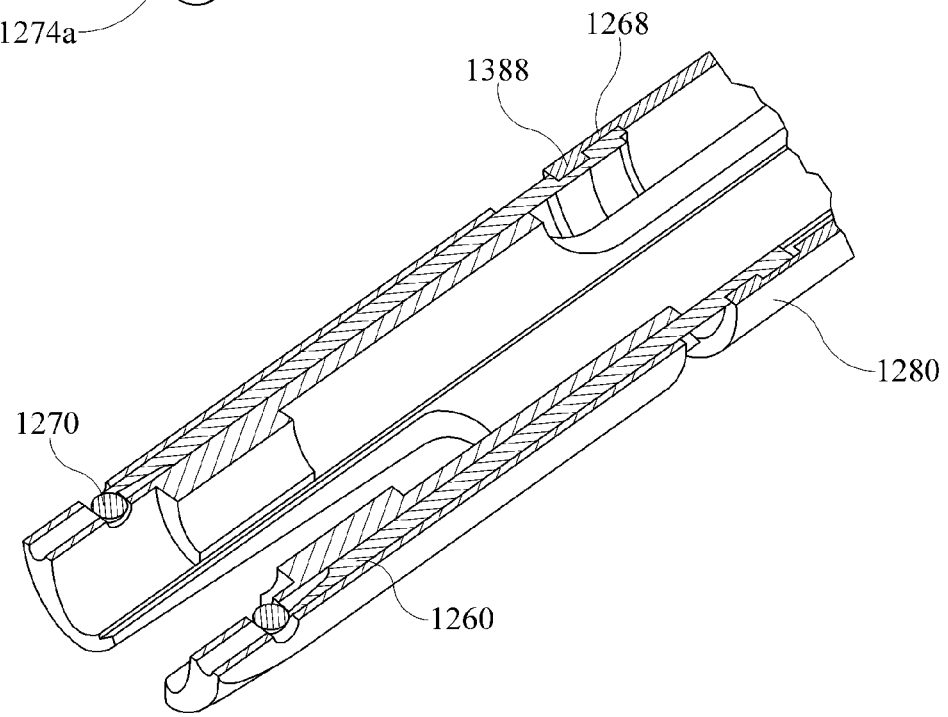
FIG. 26B is a close-up view of the embodiment shown in FIG. 25C with the long pins in a retracted position.

Referring to FIGS. 26A and 26B, the barrel subassembly 1200 may further be provided with a pair of long pins 1260 that may be somewhat generally cylindrical and may reside in corresponding longitudinal openings 1262 in the wall of a portion of barrel subassembly 1200. The long pins 1260 may have distal ends that have a taper 1264. The taper 1264 may be suitable to determine the position or allowable position of balls 1270, and may be suitable to advance the balls 1270 by a wedging action.

The balls 1270 may reside within and between the openings 1274a, 1274b in the barrel subassembly 1200. A more exteriorly-located opening 1274b may be located to connect an outer surface of the barrel subassembly with a longitudinal opening 1262. The more exteriorly-located opening 1274b may have an internal diameter larger than the diameter of the balls 1270, such that the balls 1270 may pass through the more exteriorly-located opening 1274b for assembly purposes.

A more interiorly-located opening 1274a may be located to connect an inner surface of the barrel subassembly with a longitudinal opening 1262. The more interiorly-located opening 1274a may have a diameter slightly smaller than the diameter of the ball 1270, so as to allow partial passage of the ball 1270 but prevent complete passage of the ball 1270 through the more interiorly-located opening 1274a.

Relevant parts may be dimensioned such that when the barrel subassembly 1200 is fully assembled, the long pins 1260 prevent escape of the balls 1270 through the more exteriorly-located opening 1274b for any allowed position of long pins 1260. This assembly arrangement is essentially a ball detent system.

The barrel subassembly 1200 may further be provided with a release sleeve 1280. The release sleeve 1280 may be tubular having a longitudinal axis generally coinciding with a longitudinal axis of the barrel subassembly 1200. Release sleeve 1280 may mechanically interact with long pins 1260 so that motion of release sleeve 1280 also causes motion of the long pins 1260. As illustrated in FIGS. 26A and 26B, tab features 1368 of the long pins 1262 engage with tab features 1388 of release sleeve 1280 to provide such translation of motion. It is also possible that the long pins 1260 might be joined to the release sleeve 1280 or could even be made integrally with the release sleeve 1280. There may be a spring 1286 disposed to urge the release sleeve 1280 to a default position. The default position may be such that the long pins 1260 are positioned to their distal extent toward the distal end 1200d of the barrel subassembly 1200, thereby forcing the balls 1270 into a protruding configuration through the interior openings 1274a for engaging with indentations 1140 on the external surface of the screw head 1110. However, the spring 1286 is not essential, nor is it necessary that any particular position of the release sleeve 1280 and the long pins 1260 be a default position.

FIG. 26A illustrates an extended configuration of the barrel subassembly 1200, in which the long pins 1260 and release sleeve 1280 are at their most distal permitted position. This position urges the balls 1270 to protrude through the opening 1274a. This configuration may permit the barrel subassembly 1200 to grip the screw head 1110 such as at the indentations 1140. FIG. 26B illustrates a retracted configuration of the barrel subassembly 1200, in which in which the long pins 1260 and the release sleeve 1280 are at their most proximal permitted position. This position retracts the long pins 1260 from the balls 1270 and permits the balls 1270 to retract into the interior openings 1274a. In this configuration, the balls 1270 may be such that the surfaces of the balls 1270 are approximately flush with the nearby internal surface of the barrel subassembly 1200. This configuration may permit the barrel subassembly 1200 to be disengaged from a screw head 1110.

The barrel subassembly 1200 may have, at its proximal end, a thread 1250 suitable to engage a corresponding adapter thread 1450 on the drive tube subassembly 1300. The barrel thread 1250 may be an internal thread cut into an adapter piece that mates with the barrel tube 1210. Alternatively, an internal thread may be cut into the barrel tube 1210. Alternatively, the barrel thread 1250 may be an external thread.

Figure 29A:
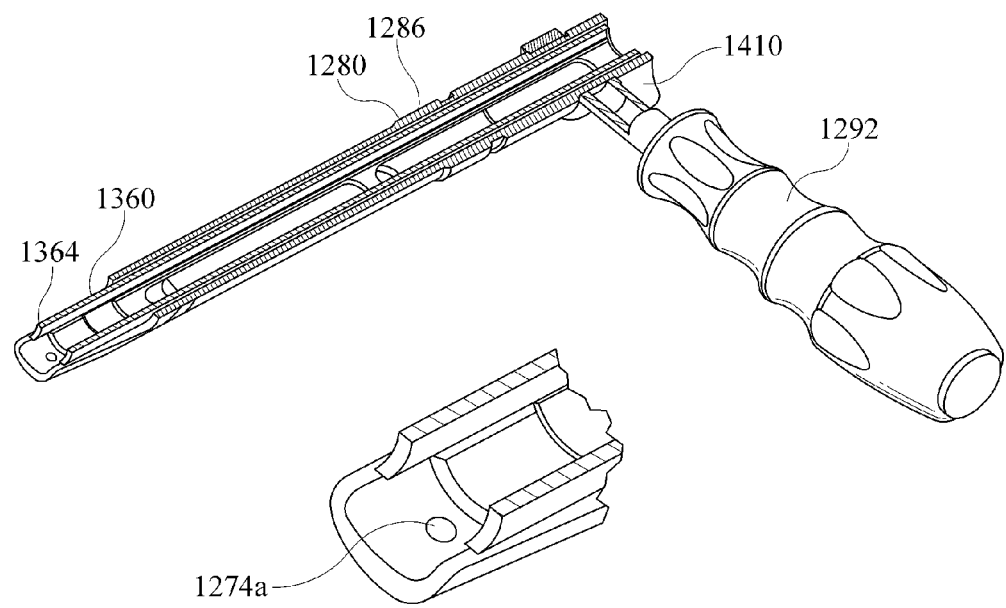
FIG. 29A is a cross-sectional view of the embodiment shown in FIG. 28, in a first configuration.
Figure 29B:
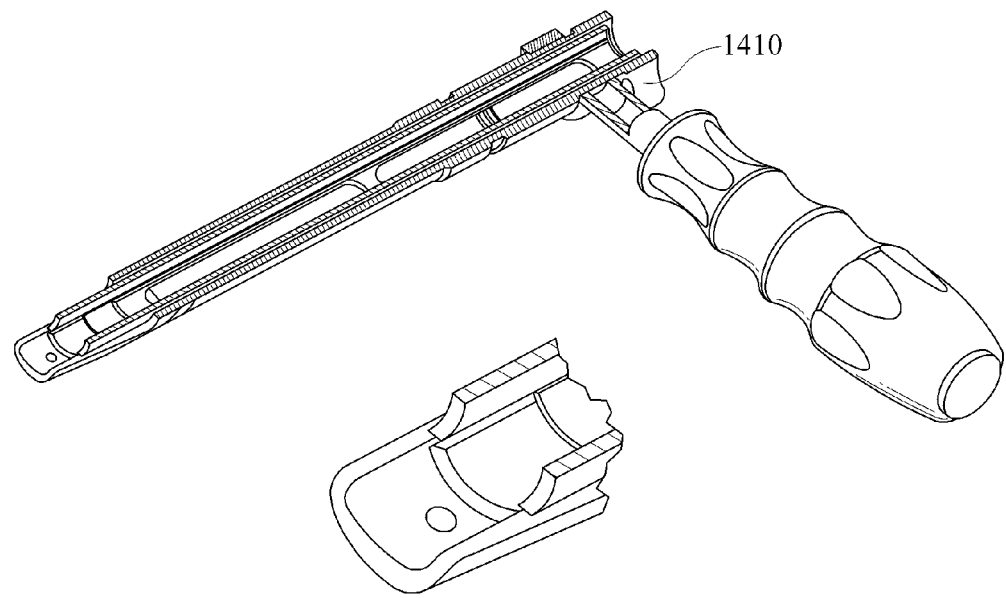
FIG. 29B is a cross-sectional view of the embodiment shown in FIG. 28, in a second configuration.

Referring to FIGS. 29A and 29B, the barrel subassembly 1200 may further have an external handle 1292 suitable for convenient gripping. The external barrel handle 1292 may be permanently attached to the barrel subassembly 1200, or may be attachable to the barrel subassembly 1200, or may simply grip around an external surface of the barrel subassembly 1200.

Figures 27, 28:
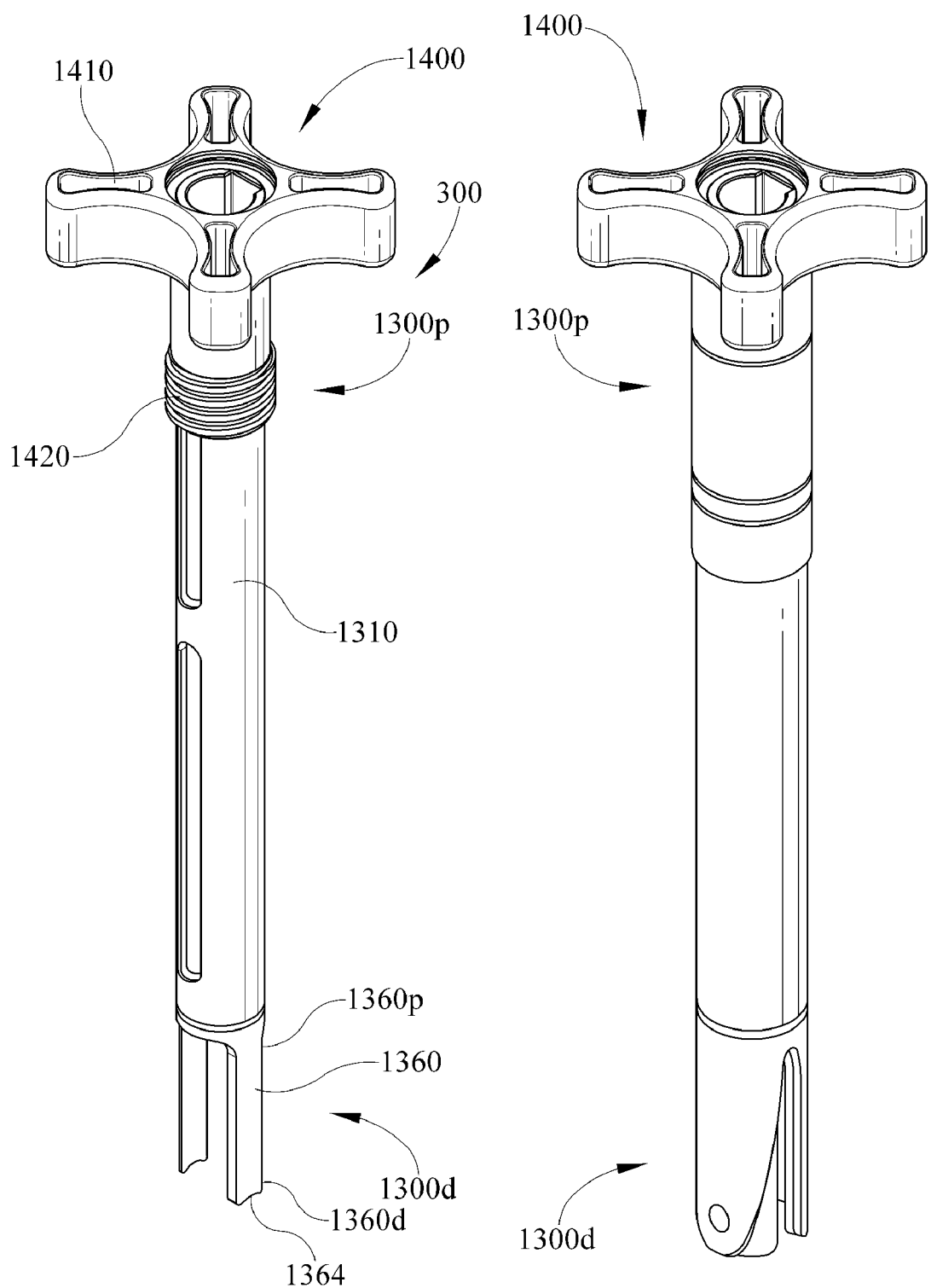
FIG. 27 is a three-dimensional perspective view of a driver subassembly.
FIG. 28 is a three-dimensional perspective view of an assembly of both a barrel subassembly and a driver subassembly.

Referring now to FIG. 27, the drive subassembly 1300 may be hollow and tubular, with a central passageway that is suitable to allow the passage therethrough of components such as a setscrew (not shown) receivable in the screw head 1110 to anchor a spinal rod 1130 to the screw 1100. The drive subassembly 1300 may be provided with a drive tube 1310. The drive subassembly 1300 may be provided with a pair of prongs 1360, which may extend distally from the drive tube 1310 and may be located 180 degrees apart from each other around the circumferential direction of the drive tube subassembly 1300. The prongs 1360 may have a proximal end 1360*p* and a distal end 1360*d*. The distal ends 360*d* of the prongs 1360 may have a concave shape 1364 such as to at least approximately match a portion of an external shape of a spinal rod 1130. The proximal end of drive subassembly 1300 may have a knob subassembly 1400 that may be connected to the drive tube 1310 in such a way that the knob subassembly 1400 may rotate with respect to the barrel subassembly 1200.

There may further be provided means for making a portion of the drive subassembly 1300, such as the drive tube 1310, non-rotatable with respect to the barrel subassembly 1200. These means may include a slot 1320 through the drive tube 1310. The drive slot 1320 may cooperate with a feature of the barrel subassembly 1200 to prevent rotation of the drive tube 1310 with respect to the barrel subassembly 1200, while still allowing the drive tube 1310 to translate with respect to the barrel subassembly 1200.

The knob subassembly 1400 may have a knob 1410 that may be connected to an adapter 1420. The adapter 1420 may be externally threaded with adapter threads 1450 so as to cooperate with the barrel threads 1250. The knob subassembly 1400 may be connected to the drive tube 1310 so as to be rotatable with respect to the drive tube 1310, but to permit little or no translation with respect to the drive tube 1310. This connection may involve a snap ring and a polymeric bushing, to retain the knob subassembly 1400 to the drive tube 1310 while allowing relative rotation. Alternatively, the adapter thread 1450 may be an internal thread as long as it cooperates with the barrel thread 1250.

Referring now to FIG. 28, there is illustrated an assembly of a barrel subassembly 1200 and a drive subassembly 1300. There is further illustrated in FIG. 29A and FIG. 29B two configurations of this assembly.

In FIG. 29A, it is illustrated that the distal tips 1364 of the prongs 1360 are at their distal extent. FIG. 29A also illustrates a distance between the centerline of the interior opening 1274*a* and the tip 1364 of the prong 1360. The surface of the knob 1410 that faces the barrel assembly 1200 is in contact with the barrel assembly 1200. In this configuration, a spinal rod 1130 may be seated in the head 1110 of screw 1100, and ready for the installation of a setscrew to lock rod 1130 in place.

In FIG. 29B, it is illustrated that the distal tips 1364 of the prongs 1360 are more proximal than were illustrated in FIG. 29A. FIG. 29B also illustrates a distance between the centerline of interior opening 1274*a* and the tip 1364 of the prong 1360, which is larger than the distance illustrated in FIG. 29A. The surface of the knob 1410 that faces the barrel subassembly 1200 does not contact the barrel subassembly, leaving a gap between the knob 4110 and the barrel subassembly 1200.

The barrel subassembly 1200 and drive subassembly 1300 may have cooperating features that allow translation of the drive subassembly 1300 through the bore of the barrel subassembly 1200, but prevent rotation of the drive subassembly 1300 with respect to barrel subassembly 1200.

The pedicle screw 1110 may be made of a suitable biocompatible material such as titanium or a titanium alloy such as Ti-6Al-4V, which may be of the Extra Low Interstitial variety. Parts of the installation tool may be made of a suitable biocompatible material such as stainless steel. It is further possible that either or both of balls 1270 and the long pins 1260 may be made of ferromagnetic or magnetizable materials and at least one of them may be magnetized, so that the balls 1270 tend to stay in contact with the long pins 1260, and the balls 1270 would retract through openings 1274*a* when the long pins 1260 are retracted. For example, series 1400 stainless steels could be used, or other magnetic materials could be used.

Referring now to FIGS. 30A through 30D, embodiments of the invention also provide methods of use of the described implant 1100.

Figure 30A:
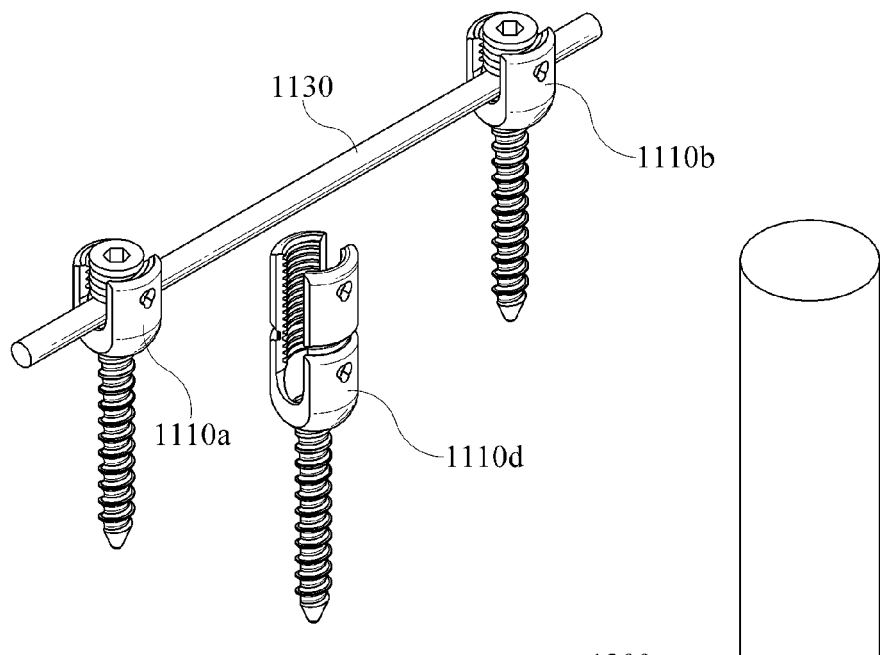
FIG. 30A is a three-dimensional illustration showing the heads of three screws that have been attached to undesirably positioned vertebrae.

FIG. 30A shows a screw head 1110*d* that has been attached to an undesirably positioned vertebra. On either side of the head 1110*d* are screw heads 1110*a*, 1110*b* that are attached to acceptably positioned vertebrae. A spinal rod 130 may then be placed between screw heads 1110*a*, 1110*b*. The spinal rod 1130 may be anchored in the screw heads 1110*a*, 110*b* using setscrews (not shown).

Figure 30B:
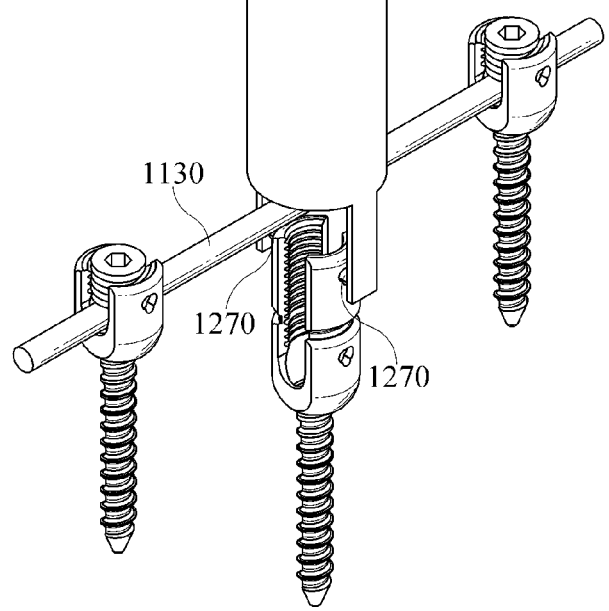
FIG. 30B is a three-dimensional illustration showing the situation of FIG. 30A with a barrel subassembly grasping a screw head.

As illustrated in FIG. 30B, a barrel subassembly 1200 may be placed such that it straddles the spinal rod 1130 and grasps the screw head 1110*d*. The grasping may be accomplished by contact of balls 1270 with indentations 1140 on opposed sides of the screw head 1110*d*.

Figure 30C:
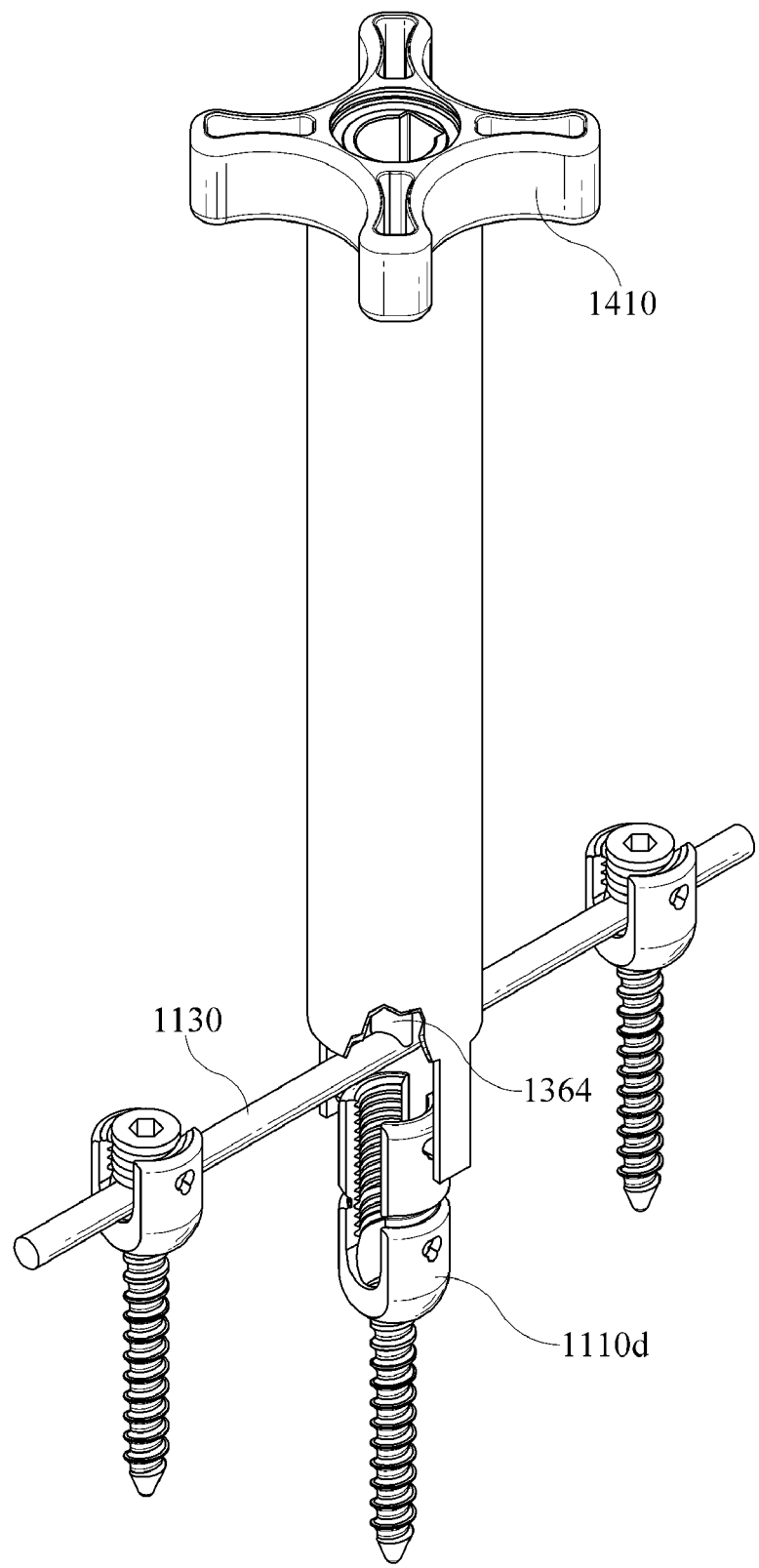
FIG. 30C is a three-dimensional illustration showing the situation of FIG. 30B with a drive subassembly placed inside the barrel subassembly and beginning to contact the spinal rod.

Referring now to FIG. 30C, the drive subassembly 1300 may be installed in the bore of barrel subassembly 1200, if it has not already been so installed. The drive subassembly 1300 may be positioned such that distal end 364 of the blade 1360 contacts the spinal rod 1130. At this point the proximal end of the drive subassembly 1300, including knob 1410, may be somewhat separated from the nearby surface of the barrel subassembly 1200.

Figure 30D:
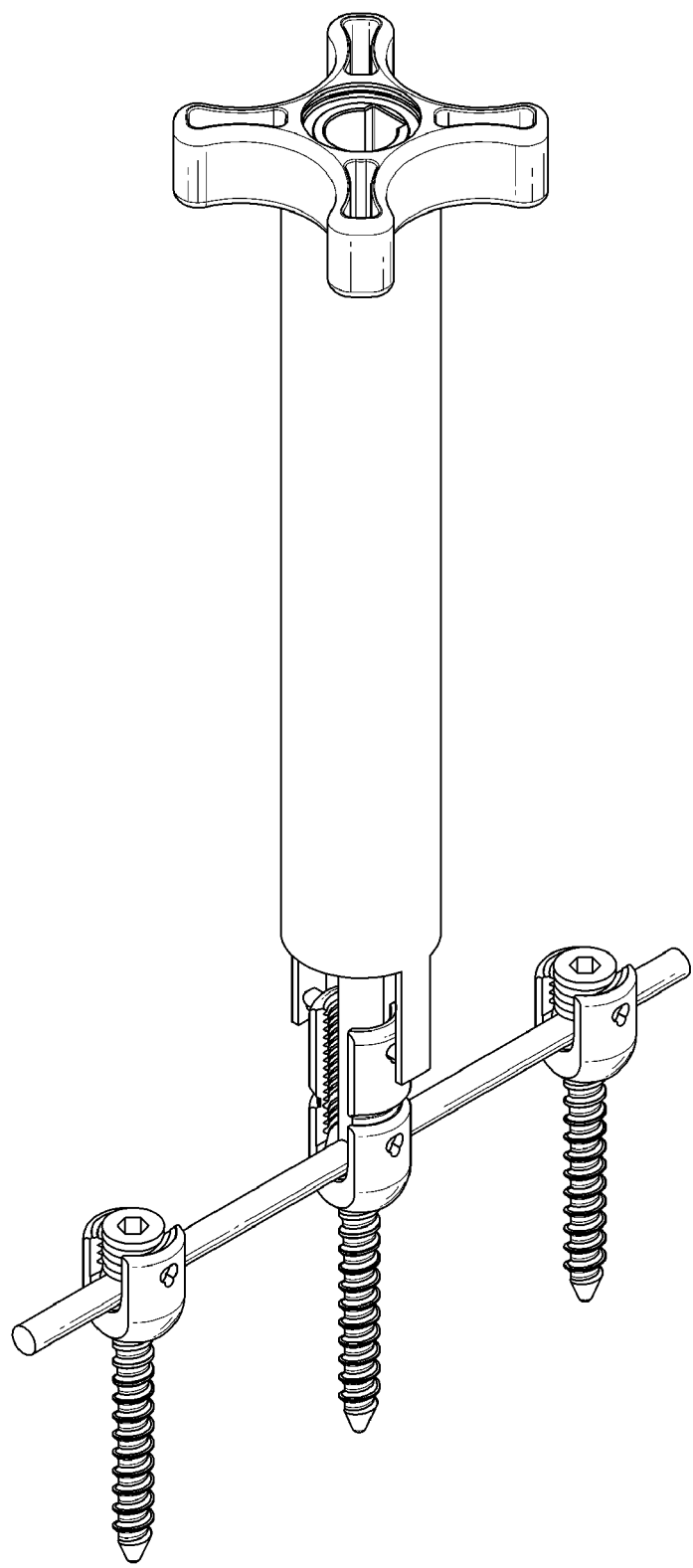
FIG. 30D shows the drive subassembly fully advanced so as to cause the spinal rod to bottom against the rod-receiving region of the screw head.

The knob 1410 may be rotated so as to advance the prongs 1360 distally relative to the barrel subassembly 1200. FIG. 30D shows the prongs 1360 fully advanced so as to cause the spinal rod 1130 to bottom against the rod-receiving region of screw head 1110*d*. At this point, a setscrew may be provided through the bore of the drive subassembly 1300, and the spinal rod 1130 may be locked in place in screw head 1110*d*. Then, the drive subassembly 1300 and the barrel subassembly 1200 may be removed from the operating region, either together or individually.

Figure 31A:
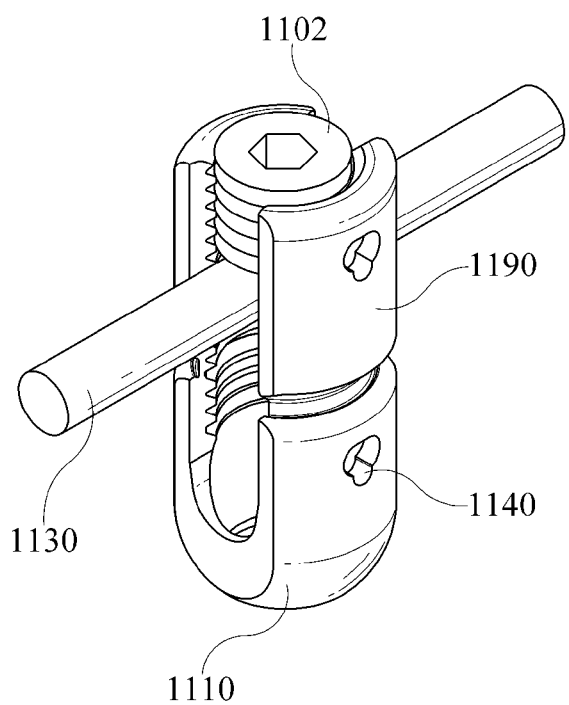
FIG. 31A illustrates a setscrew placed between tabs 190 and used to begin to urge a spinal rod toward the bottom of a receiving region of a screw head.
Figure 31B:
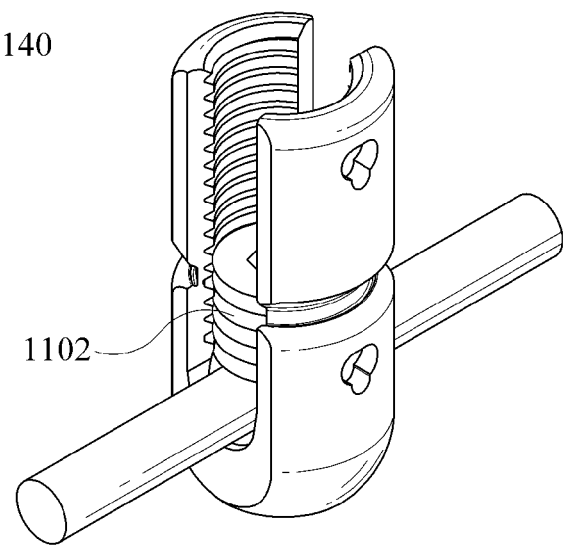
FIG. 31B shows the setscrew fully advanced so that a spinal rod has bottomed out against the bottom of a receiving region of a screw head.
Figure 31C:
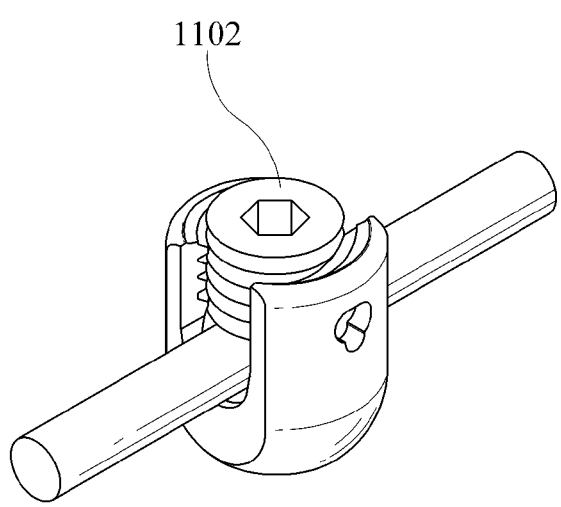
FIG. 31C shows the screw head after removal of the tabs.

Referring now to FIGS. 31A-31C, it may be appreciated that it is possible to exert force on a spinal rod 1130 through the use of a thread inside a screw head 1110 having an extended length due to the presence of tabs 1190. FIG. 31A illustrates a setscrew 1102 placed between tabs 1190 and used to begin to urge the spinal rod 1130 toward the bottom of the receiving region of screw head 1110. In FIG. 31B, the setscrew 1102 has been fully advanced so that spinal rod has bottomed out against the bottom of the receiving region of the screw head 1110. In FIG. 31C, the tabs 1190 have been removed from the screw head 1110.

Of course, it is also possible that some combination of these two force exertion methods can be used, i.e., some motion of the spinal rod 1130 and screw head 110 toward each other could be caused by advancement of the setscrew relative to screw head 1110, and some motion could be caused by advancement of drive subassembly 1300 relative to barrel subassembly 1200.

The balls 1270 are illustrated as means for the barrel assembly 1200 to interact with the indentations 140 in the screw head 1110, but it can be understood that other designs, such as cylindrical shapes, are also possible. It is also possible for the balls to be oblong about one or more axes. The long pins 1260 might be contained in a configuration other than openings 1262, as long as adequate guidance of motion is provided to long pins 1260. Either of the barrel threads 1250 or adapter threads 1450, which together form engagement between the barrel subassembly 1200 and the drive subassembly 1300, could be internal or external, with the other thread being the opposite.

It is also be possible to use the described instrument with pedicle screws that do not have break-away tabs.

All referenced documents are incorporated by reference herein in their entirety. Features described herein may be combined in any combination. Process steps may be performed in any sequence that is physically possible. Although the invention has been described herein, it is desired that the scope be limited only by the scope of the claims.

The invention claimed is:

1. A screw for use in spinal surgery, comprising:
a screw shaft;
a screw head; and
at least one extension tab extending proximally from said screw head,
said extension tab being defined relative to said screw head by a stress concentration feature,
said extension tab having a proximal end and an opposing distal portion, said extension tab tapers from said stress concentration feature at said distal portion to said proximal end wherein said extension tab at said proximal end is smaller than said extension tab at said distal portion thereof.

2. The screw of claim 1, wherein said stress concentration feature is a groove.

3. The screw of claim 1, wherein said screw shaft is integral with said screw head.

4. The screw of claim 1, wherein said screw shaft has a shaft head, and said screw head cooperates with said shaft head so as to permit a defined amount of angular movement of said screw head relative to said screw shaft.

5. A screw for use in spinal surgery, comprising:
a screw shaft;
a screw head having a longitudinal axis along a length thereof; and
at least one extension tab extending from said screw head,
said extension tab being defined relative to said screw head by an external stress concentration feature,
wherein said external stress concentration feature includes an undercut axially recessed along said longitudinal axis relative to a top surface of said screw head adjacent said extension tab wherein said at least one extension tab extends from said undercut.

6. The screw of claim 5, wherein said screw shaft is integral with said screw head.

7. The screw of claim 5, wherein said screw shaft has a shaft head, and said screw head cooperates with said shaft head so as to permit a defined amount of angular movement of said screw head relative to said screw shaft.

8. A screw for use in spinal surgery, comprising:
a screw shaft;
a screw head having a longitudinal axis and a radial axis perpendicular to said longitudinal axis; and
at least one extension tab extending from said screw head,
said extension tab being defined relative to said screw head by an external stress concentration feature,
wherein, in a planar cross-section taken in a plane passing through a longitudinal axis of said screw head, said external stress concentration feature has a profile,
wherein said profile has a proximal edge and a distal edge, and said distal edge has a most proximal portion and second portion, said second portion is at a location more radially inward than a radial location of said most proximal portion, and said second portion of said distal edge is more distal than said most proximal portion.

9. The screw of claim 8, further comprising an internal stress concentration feature positioned more distally than said external stress concentration feature along said longitudinal axis, wherein said internal stress concentration feature is axisymmetric.

10. A screw for use in spinal surgery, comprising:
a screw shaft;
a screw head having a longitudinal axis; and
at least one extension tab extending proximally along said longitudinal axis from said screw head,
said extension tab being defined relative to said screw head by a stress concentration feature,
said extension tab having a proximal end and a distal end and a tool connection feature between said proximal end and said distal end, wherein said distal end of said extension tab is adjacent said stress concentration feature, said extension tab tapers from a position more distal than said tool connection feature towards said proximal end, wherein said extension tab at said proximal end is smaller than said extension tab at said position thereof.

11. The screw of claim 10, wherein said extension tab tapers from said stress concentration feature to said proximal end.

12. The screw of claim 10, wherein said tool connection feature is one or more external indentations.

13. A screw for use in spinal surgery, comprising:
a screw shaft;
a screw head; and
at least one extension tab extending proximally from said screw head,
said extension tab being internally threaded,
said extension tab being defined relative to said screw head by a stress concentration feature, and said extension tab formed by a cutting plane intersecting said extension tab creating a taper wherein a proximal end of said extension tab is smaller than a distal end of said extension tab; and
said cutting plane intersects said internal thread of said extension tab.

14. The screw of claim 13, wherein said cutting plane intersects said stress concentration feature.

15. A screw for use in spinal surgery, comprising:
a screw shaft;
a screw head defining a longitudinal screw head axis and having a distal end adjacent said screw shaft and a proximal end opposite thereto, wherein said proximal end of said screw head includes a top surface with an undercut, said undercut further comprising a groove extending circumferentially around said top surface and extending axially along said longitudinal screw head axis in a first direction from said top surface towards said distal end, wherein said groove includes a bottom; and at least one break-away extension tab projecting from said groove bottom in a second direction opposite said first direction.

16. The screw of claim 15, wherein said at least one break-away extension tab decreases in size in said second direction away from said groove bottom.

17. The screw of claim 15, wherein a first distance from said screw head distal end to said screw head top surface is larger than a second distance from said screw head distal end to said groove bottom.

18. The screw of claim 17, wherein said screw head further comprises an internal stress concentration feature, said internal stress concentration feature is axisymmetric and positioned at a third distance from said screw head distal end, wherein said third distance is smaller than said second distance.

* * * * *